US012648771B2

(12) United States Patent
Bahoora et al.

(10) Patent No.: US 12,648,771 B2
(45) Date of Patent: Jun. 9, 2026

(54) PUSH-IN SUTURE ANCHOR SYSTEM

(71) Applicant: Response Arthroscopy, Inc.,
Minneapolis, MN (US)

(72) Inventors: Kimberly Bahoora, Medina, MN (US);
Jacob Hustedt, Sandy, UT (US);
Douglas Kohrs, Minneapolis, MN (US)

(73) Assignee: Responsive Arthroscopy, Inc.,
Minneapolis, MN (US)

( * ) Notice: Subject to any disclaimer, the term of this
patent is extended or adjusted under 35
U.S.C. 154(b) by 175 days.

(21) Appl. No.: 18/335,914

(22) Filed: Jun. 15, 2023

(65) Prior Publication Data

US 2023/0320721 A1     Oct. 12, 2023

Related U.S. Application Data

(63) Continuation     of     application     No.
PCT/US2022/076334, filed on Sep. 13, 2022.
(Continued)

(51) Int. Cl.
*A61B 17/04*     (2006.01)
(52) U.S. Cl.
CPC .. *A61B 17/0401* (2013.01); *A61B 2017/0409*
(2013.01); *A61B 2017/0414* (2013.01);
(Continued)
(58) Field of Classification Search
CPC ........ A61B 17/0401; A61B 2017/0409; A61B
2017/0406; A61B 2017/0403; A61B 2017/0412; A61B 2017/0414; A61B
2017/0427; A61B 2017/0438; A61B
2017/044; A61B 2017/0441;
(Continued)

(56) References Cited

U.S. PATENT DOCUMENTS 545,760 A     9/1895   Ashley
3,845,575 A   11/1974  Boden
(Continued)

FOREIGN PATENT DOCUMENTS

EP     3138505 A1 *  3/2017   ......... A61B 17/0401
EP     3235471 A1   10/2017
(Continued)

OTHER PUBLICATIONS

PCT ISR for PCT/US22/76334 (Year: 2022).*
(Continued)

*Primary Examiner* — Katherine Shi
(74) *Attorney, Agent, or Firm* — Goodwin Procter LLP

(57)     ABSTRACT
Improved suture anchor systems and methods of use are
disclosed herein. The suture anchor may have proximal and
distal ends, and first and second lateral sides extending
between the proximal end and the distal end. A centrally
located suture passage may extend through the anchor body
from a first opening in the first lateral side to a second
opening in the second lateral side. A channel may extend
along a longitudinal axis of the anchor body. The insert may
be configured to translate longitudinally within the channel
between the proximal end of the anchor body and the distal
surface of the suture passage. There may also be provided a
surgical broach adapted for use with the suture anchor
system.

19 Claims, 18 Drawing Sheets

Related U.S. Application Data

(60) Provisional application No. 63/244,038, filed on Sep. 14, 2021.

(52) U.S. Cl.
CPC . *A61B 2017/0425* (2013.01); *A61B 2017/044* (2013.01); *A61B 2017/0456* (2013.01); *A61B 2017/0458* (2013.01)

(58) Field of Classification Search
CPC .... A61B 2017/0445; A61B 2017/0446; A61B 2017/0448; A61B 2017/045; A61B 2017/0451; A61B 2017/0453; A61B 2017/0456; A61B 2017/0459
See application file for complete search history.

(56) References Cited

U.S. PATENT DOCUMENTS

| | | | |
|---|---|---|---|
| 3,953,144 A | 4/1976 | Boden | |
| 6,185,798 B1 | 2/2001 | Ton | |
| 6,585,730 B1 | 7/2003 | Foerster | |
| 7,637,926 B2 | 12/2009 | Foerster et al. | |
| 7,713,286 B2 * | 5/2010 | Singhatat | A61B 17/0401 606/232 |
| 8,100,923 B2 | 1/2012 | Paraschac et al. | |
| 8,133,258 B2 | 3/2012 | Foerster et al. | |
| 8,162,978 B2 | 4/2012 | Lombardo et al. | |
| 8,371,004 B2 | 2/2013 | Huber et al. | |
| 8,409,252 B2 | 4/2013 | Lombardo et al. | |
| 8,652,173 B2 | 2/2014 | Mansmann | |
| 8,790,346 B2 | 7/2014 | Daniels et al. | |
| 9,168,034 B2 | 10/2015 | Lombardo et al. | |
| 9,226,742 B2 | 1/2016 | Wolf et al. | |
| 9,241,706 B2 | 1/2016 | Paraschac et al. | |
| 9,277,910 B2 | 3/2016 | Nason et al. | |
| 9,295,460 B2 | 3/2016 | Hoof et al. | |
| 9,345,467 B2 | 5/2016 | Lunn et al. | |
| 9,402,617 B2 | 8/2016 | Baird | |
| 9,463,010 B2 | 10/2016 | Gittings et al. | |
| 9,687,224 B2 | 6/2017 | Lunn et al. | |
| 9,936,939 B2 | 4/2018 | Nguyen et al. | |
| 10,076,377 B2 | 9/2018 | Bonutti et al. | |
| 10,159,477 B2 | 12/2018 | Lunn et al. | |
| 10,238,377 B2 | 3/2019 | Nason et al. | |
| 11,298,120 B2 | 4/2022 | Bowman et al. | |
| 11,510,665 B2 | 11/2022 | Hustedt | |
| 12,178,425 B2 | 12/2024 | Hustedt | |
| 2003/0195563 A1 | 10/2003 | Foerster | |
| 2005/0119663 A1 | 6/2005 | Keyer et al. | |
| 2006/0265010 A1 | 11/2006 | Paraschac et al. | |
| 2006/0282119 A1 | 12/2006 | Perchik | |
| 2007/0060922 A1 | 3/2007 | Dreyfuss | |
| 2007/0162033 A1 | 7/2007 | Daniels et al. | |
| 2007/0213770 A1 | 9/2007 | Dreyfuss | |
| 2007/0276437 A1 | 11/2007 | Call et al. | |
| 2008/0051836 A1 | 2/2008 | Foerster et al. | |
| 2008/0275469 A1 | 11/2008 | Fanton et al. | |
| 2008/0294204 A1 | 11/2008 | Chirico et al. | |
| 2009/0012522 A1 | 1/2009 | Lob | |
| 2009/0012571 A1 | 1/2009 | Perrow et al. | |
| 2009/0082807 A1 * | 3/2009 | Miller | A61B 17/0401 606/232 |
| 2009/0292321 A1 | 11/2009 | Collette | |
| 2009/0312794 A1 * | 12/2009 | Nason | A61B 17/0401 606/232 |
| 2010/0004683 A1 | 1/2010 | Hoof et al. | |
| 2011/0004242 A1 * | 1/2011 | Stchur | A61B 17/0401 606/232 |
| 2011/0009885 A1 | 1/2011 | Graf et al. | |
| 2011/0112576 A1 * | 5/2011 | Nguyen | A61B 17/0401 606/232 |
| 2011/0166599 A1 | 7/2011 | Jervis et al. | |
| 2011/0238113 A1 | 9/2011 | Fanton et al. | |
| 2012/0123474 A1 | 5/2012 | Zajac et al. | |
| 2013/0030479 A1 | 1/2013 | Regauer | |
| 2013/0123841 A1 | 5/2013 | Lyon | |
| 2013/0144334 A1 | 6/2013 | Bouduban et al. | |
| 2013/0197578 A1 | 8/2013 | Gregoire et al. | |
| 2014/0081323 A1 | 3/2014 | Hawkins | |
| 2014/0257294 A1 | 9/2014 | Gedet et al. | |
| 2014/0379028 A1 | 12/2014 | Lo | |
| 2016/0030035 A1 | 2/2016 | Zajac et al. | |
| 2016/0089131 A1 | 3/2016 | Wade | |
| 2016/0100833 A1 | 4/2016 | Lunn et al. | |
| 2016/0157852 A1 * | 6/2016 | Dougherty | A61B 17/0483 606/232 |
| 2016/0235398 A1 | 8/2016 | Nguyen et al. | |
| 2016/0302785 A1 | 10/2016 | Nason et al. | |
| 2017/0065273 A1 | 3/2017 | Hart et al. | |
| 2017/0189007 A1 | 7/2017 | Burkhart et al. | |
| 2017/0303910 A1 * | 10/2017 | Niver | A61B 17/0401 |
| 2018/0008256 A1 * | 1/2018 | Fallin | A61B 90/06 |
| 2018/0146959 A1 * | 5/2018 | Gerber | A61B 17/0401 |
| 2018/0249998 A1 | 9/2018 | Chavan et al. | |
| 2018/0368827 A1 | 12/2018 | Balboa et al. | |
| 2019/0038275 A1 * | 2/2019 | Clark | A61B 17/0401 |
| 2019/0117377 A1 | 4/2019 | Ticker | |
| 2019/0167254 A1 | 6/2019 | Balboa et al. | |
| 2019/0175223 A1 | 6/2019 | Nguyen et al. | |
| 2019/0343507 A1 | 11/2019 | Chavan et al. | |
| 2019/0380695 A1 | 12/2019 | Fallin et al. | |
| 2019/0380747 A1 | 12/2019 | Fischer et al. | |
| 2020/0077999 A1 | 3/2020 | Bowman et al. | |
| 2020/0245997 A1 * | 8/2020 | Balboa | A61B 17/0401 |
| 2020/0337690 A1 | 10/2020 | Smith | |
| 2022/0054122 A1 * | 2/2022 | Bowman | A61B 17/0401 |
| 2022/0167963 A1 | 6/2022 | Hustedt | |
| 2022/0192655 A1 | 6/2022 | Bowman et al. | |
| 2023/0210516 A1 | 7/2023 | Hustedt | |
| 2023/0320720 A1 | 10/2023 | Bahoora et al. | |

FOREIGN PATENT DOCUMENTS

| | | | |
|---|---|---|---|
| WO | WO-2020018751 A1 * | 1/2020 | A61B 17/0485 |
| WO | WO-2020056029 A1 | 3/2020 | |
| WO | WO-2021202123 A1 | 10/2021 | |
| WO | WO-2022039991 A1 | 2/2022 | |
| WO | WO-2023044295 A1 | 3/2023 | |

OTHER PUBLICATIONS

PCT/US2019/050659 International Search Report dated Dec. 31, 2019.

PCT/US2021/023101 International Search Report and Written Opinion mailed Jun. 24, 2021.

PCT/US2021/045506 International Search Report and Written Opinion dated Jan. 31, 2022.

PCT/US2022/076334 International Search Report and Written Opinion mailed Dec. 13, 2022.

* cited by examiner

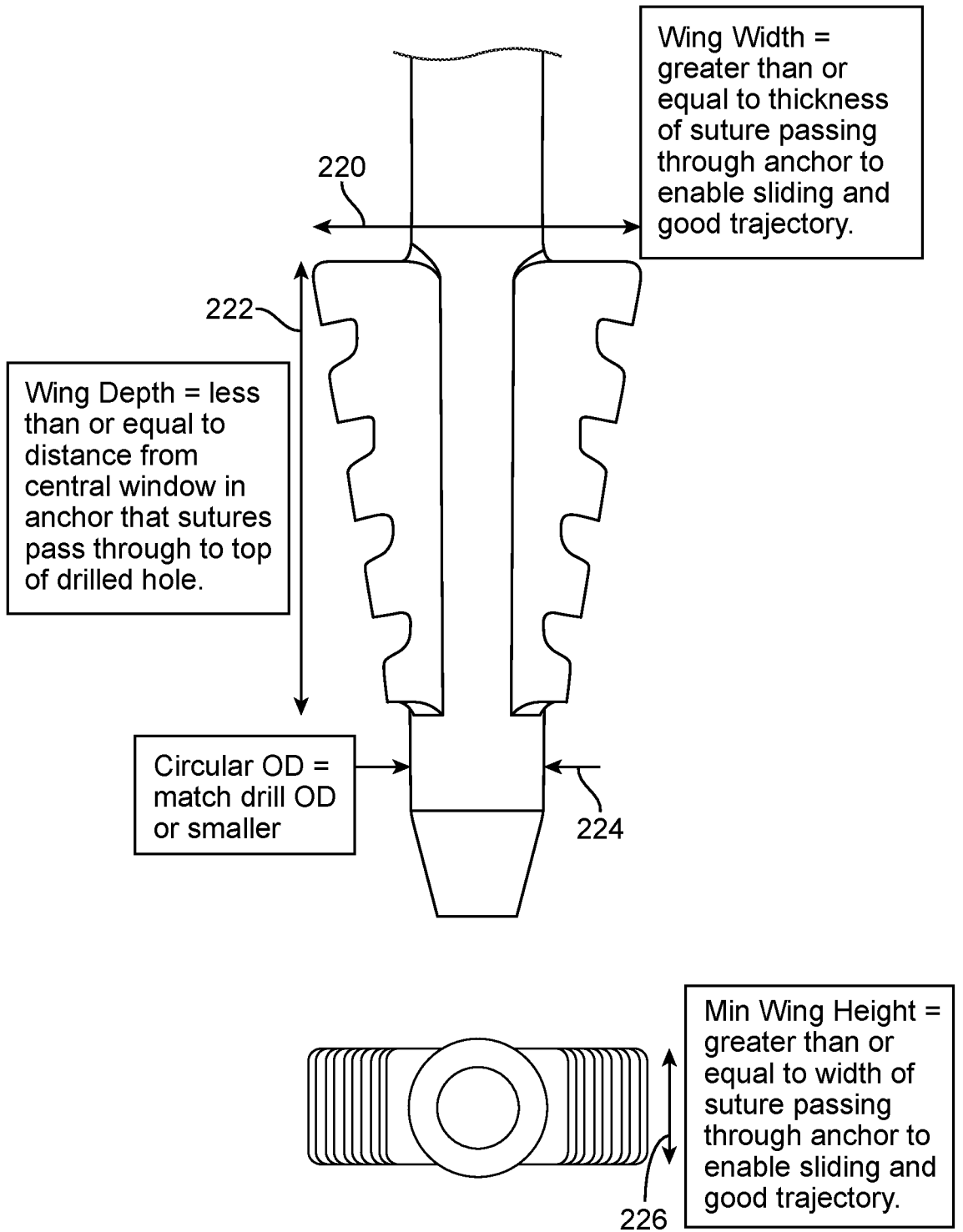

Wing Width = greater than or equal to thickness of suture passing through anchor to enable sliding and good trajectory.

220

222

Wing Depth = less than or equal to distance from central window in anchor that sutures pass through to top of drilled hole.

Circular OD = match drill OD or smaller

224

Min Wing Height = greater than or equal to width of suture passing through anchor to enable sliding and good trajectory.

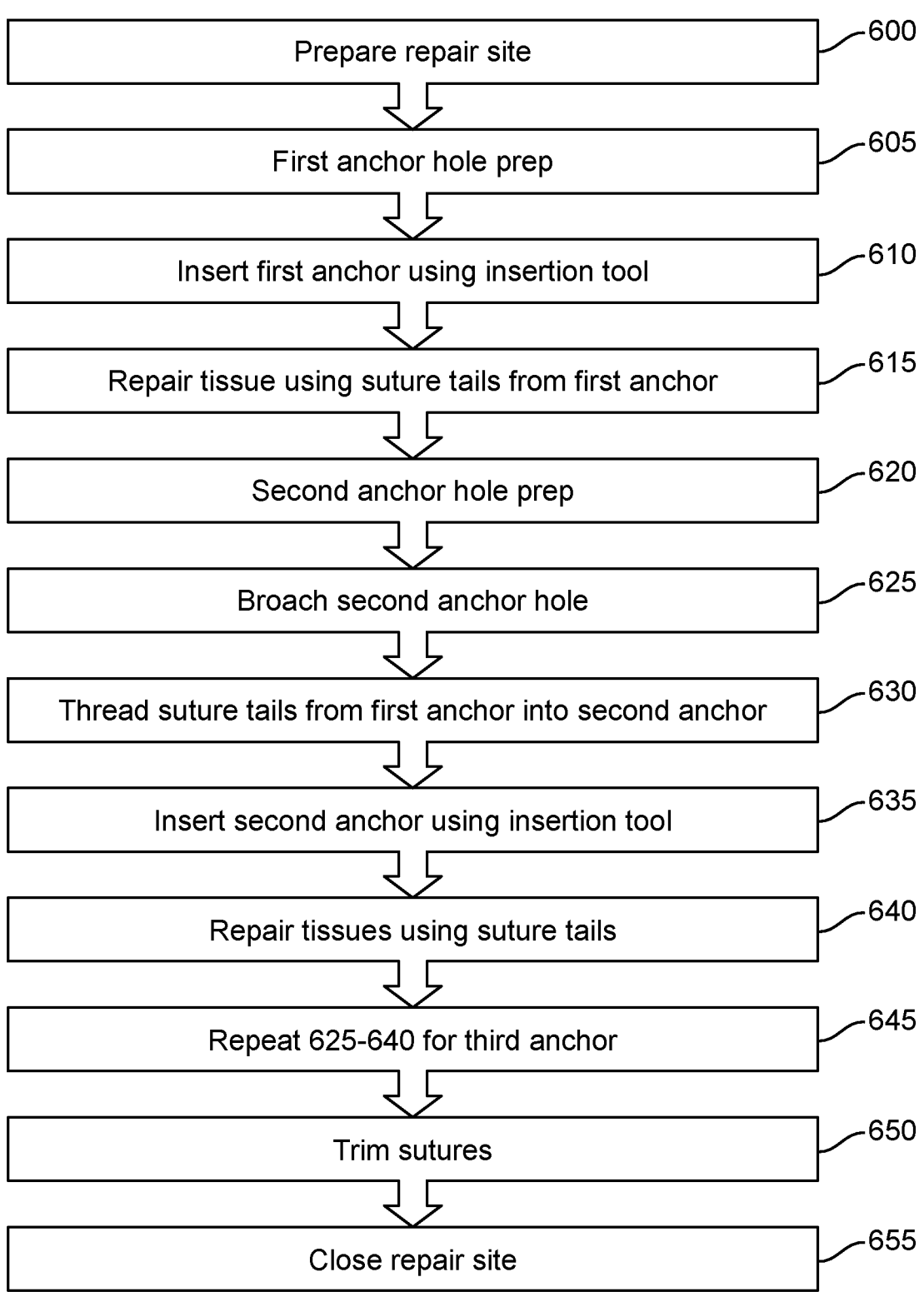

| | |
|---|---|
| Prepare repair site | 600 |
| First anchor hole prep | 605 |
| Insert first anchor using insertion tool | 610 |
| Repair tissue using suture tails from first anchor | 615 |
| Second anchor hole prep | 620 |
| Broach second anchor hole | 625 |
| Thread suture tails from first anchor into second anchor | 630 |
| Insert second anchor using insertion tool | 635 |
| Repair tissues using suture tails | 640 |
| Repeat 625-640 for third anchor | 645 |
| Trim sutures | 650 |
| Close repair site | 655 |

FIG. 6

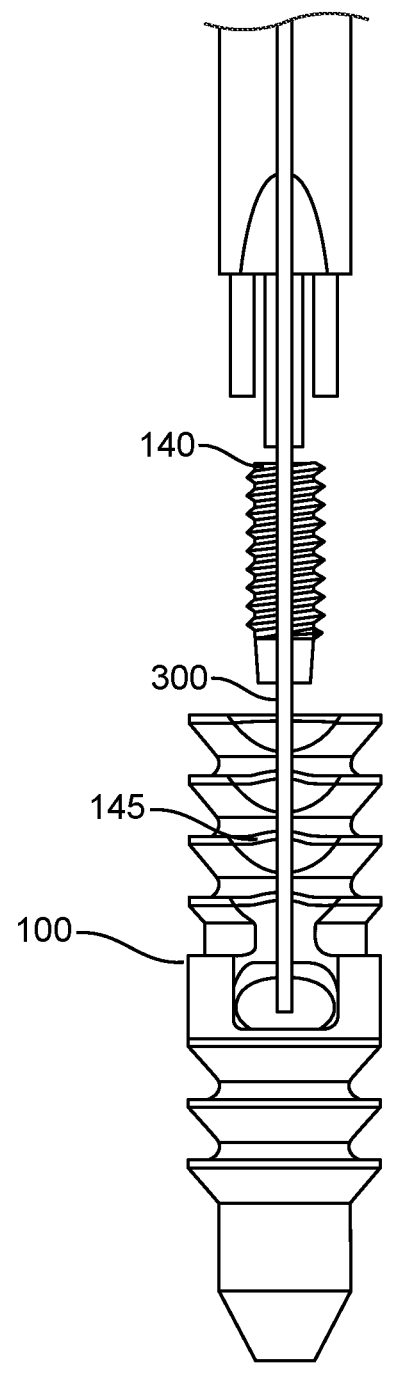
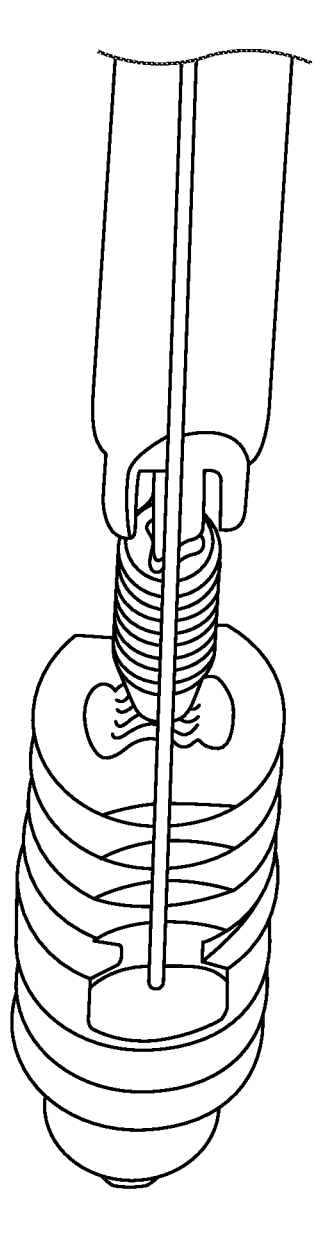
FIG. 9

PUSH-IN SUTURE ANCHOR SYSTEM

CROSS-REFERENCE TO RELATED APPLICATIONS

This application is a continuation of International Application No. PCT/US2022/076334 titled "Improved Push-in Suture Anchor System" and filed on Sep. 13, 2022, which claims the benefit and priority to U.S. Provisional Patent Application No. 63/244,038 titled "Push-in Suture Anchor System" and filed on Sep. 14, 2021, which is hereby incorporated by reference herein in its entirety.

BACKGROUND

The complete or partial detachment of ligaments, tendons, and/or other soft tissues from their associated bones within the body are relatively commonplace injuries, particularly among athletes. Tissue detachment may occur as the result of an accident such as a fall, over-exertion during a work-related activity, during the course of an athletic event, or in any one of many other situations and/or activities.

In the case of a partial detachment, the injury will frequently heal itself, if given sufficient time and if care is taken not to expose the injury to further undue stress. In the case of complete detachment, however, surgery may be needed to re-attach the soft tissue to its associated bone or bones. Suture anchors provide one type of device that may be used in helping to re-attach soft tissue to its associated bone or bones.

While suture anchors have been used to anchor tissue to bone, the sutures utilized in the surgery are themselves prone to failure in the years following the surgery as they are subjected to repeated movements. The sutures utilized to secure the soft tissue to the bone will weaken, fray, and eventually break, leading to a total failure of the surgery, and a negative patient outcome.

Similarly, suture anchors themselves are also known to be prone to failure in the years following the surgery as they are subjected to repeated movement and pulling upon the anchor by the suture and the tissues to which the suture is attached. The suture anchor may shift within the bone and begin to pull out, causing pain, surgical failure, and a negative patient outcome. Such negative patient outcomes generally require a subsequent surgery to correct, often with a comparatively more invasive procedure utilizing a larger anchor, which may require the removal of additional bone.

SUMMARY

The present disclosure generally relates to improved suture anchors and associated methods for using the improved suture anchors in attaching soft tissue to their associated bone or bones.

During surgeries where soft tissue is attached to its associated bone or bones, it is generally beneficial to be able to secure anchored suture material using tension, such as by tying a knot. However, in many situations, it is difficult for a surgeon to form a knot and thus it is beneficial to provide knotless suture anchors. While knotless suture anchors allow for surgeons to more easily secure suture materials, knotless suture anchors that are currently available often fail to provide a method for a surgeon to apply tension to the suture in the way that one may apply tension by forming a knot. As such, it would be beneficial to provide a knotless suture anchor that allows a surgeon to apply an amount of tension, comparable to that of a knot, in the securing of the suture material to the bone. It is also desirable to provide suture anchors that are suitable for use with sutures tied into knots as well, such that a single suture anchor design may accommodate the various embodiments and preferences. Accordingly, suture anchors, suture anchor systems, and methods of using the same are provided to address this need.

It is also appreciated by the inventors that it is desirable to design a suture anchor system which will increase the lifespan of the suture and suture anchor system by limiting the surface interactions between the suture and the suture anchor. Embodiments of improved suture anchors that are discussed herein have been designed to preserve integrity of the suture when in use. Some embodiments may comprise smooth or rounded edges on one or more anchor surfaces, and centrally located passages which reduce displacement between the distal end of a suture and tissues attached thereto, which may reduce friction placed on the suture by the anchor.

Aspects disclosed herein provide a suture anchor system, an exemplary system comprising an anchor body having a proximal end, a distal end, a longitudinal axis, a first lateral side extending between the proximal end and the distal end, and a second lateral side extending between the proximal end and the distal end and opposite laterally of the first lateral side; a suture passage comprising a proximal surface and a distal surface and extending through the anchor body from a first opening in the first lateral side to a second opening in the second lateral side, where the suture passage is positioned approximately halfway between the proximal end and the distal end of the anchor body; a plurality of distal ridges disposed on the anchor body, wherein the plurality of distal ridges is proximal to the distal end and distal to the suture passage; one or more proximal ridges disposed on the anchor body, wherein the one or more proximal ridges is distal to the proximal end and proximal to the suture passage; a channel extending along the longitudinal axis of the anchor body from a proximal opening in the proximal end of the anchor body to a distal opening in the proximal surface of the suture passage, and an insert comprising an insert body having a proximal end and a distal end, wherein the insert is configured to translate longitudinally within the channel between the proximal end of the anchor body and the distal surface of the suture passage. In some embodiments, the channel may not extend past the distal surface of the suture passage. In some embodiments, the anchor may further include an insert comprising an insert body having a proximal end and a distal end, where the insert is configured to translate longitudinally within the channel between the proximal end of the anchor body and the distal surface of the suture passage.

In some embodiments, the first lateral side and the second lateral side may be positioned adjacent to one another. In some embodiments, the first lateral side and the second lateral side may be positioned opposite one another. In some embodiments, an angle between the first lateral side and the second lateral side is 90 degrees. In some embodiments, an angle between the first lateral side and the second lateral side is 180 degrees.

In some embodiments, the suture passage is approximately halfway between the proximal end and the distal end of the anchor body. In some embodiments, the suture passage is at least ⅓ of the way up the anchor body measured from the distal end of the anchor body. In some embodiments, the suture passage is approximately ⅔ of the way up the anchor body measured from the distal end of the anchor body.

In some embodiments, the suture anchor system comprises a suture. In some embodiments, the suture comprises: a #2 UHMWPE braided suture; a suture tape; a flat braid configuration; a round to flat braid configuration; a 2.3 mm round to flat tape suture; a tapered tail; a nonabsorbable material, polyester, an absorbable material, or polyglactin (PGLA).

In some embodiments, the channel comprises a threaded region along at least a portion of an interior surface of the channel.

In some embodiments, the anchor body may be defined by a plurality of segments along the longitudinal axis. In some embodiments, the plurality of segments may further include bone engaging ridges.

In some embodiments, the insert may include an insert body having a proximal end and a distal end, wherein the insert is configured to translate longitudinally within the channel between the proximal end of the anchor body and the distal surface of the suture passage. In some embodiments, the anchor body may be defined by a plurality of segments along the longitudinal axis.

In many embodiments, the distal surface of the suture passage is v-shaped and has a first lateral plane extending from the first opening towards a central normal plane and a second lateral plane extending from the second opening towards the central normal plane, the central normal plane being substantially perpendicular to the longitudinal axis of the anchor body. In many embodiments, the distal surface of the suture passage is substantially flat and substantially perpendicular to the longitudinal axis of the anchor body. In many embodiments, the distal surface of the suture passage is substantially flat and substantially perpendicular to the longitudinal axis of the anchor body.

In many embodiments, at least a portion of the distal surface of the suture passage comprises a convex curvature extending proximally towards the distal opening of the channel. In many embodiments, a proximal portion of the convex curvature extends into the distal opening of the channel. In many embodiments, the convex curvature spans the entire distal surface. In many embodiments, the convex curvature has an arc angle within a range of about 3.5° to about 15°.

In many embodiments, the distal end of the insert is shaped to correspond to the distal surface of the suture passage. In many embodiments, the distal end of the insert is rounded. In many embodiments, the distal end of the insert has a curved outer boundary.

In many embodiments, the distal end of the insert is v-shaped. In many embodiments, the distal end of the insert has a dimpled distal surface. In many embodiments, the first opening or the second opening has a polygonal shape. In many embodiments, the polygonal shape is a triangle, a quadrilateral, a pentagon, a hexagon, an octagon, a nonagon, or a decagon. In many embodiments, at least a portion of an inner surface of the channel comprises threading and at least a portion of an outer surface of the insert body comprises correspondingly-shaped threading such that longitudinal translation of the insert occurs when the insert is rotated relative to the channel.

In many embodiments, at least a portion of the inner surface of the channel is not threaded. In many embodiments, the insert body is configured to be press fit into the channel. In many embodiments, the anchor or the insert further comprises a locking mechanism configured to lock the insert in the channel. In many embodiments, the locking mechanism comprises a ratchet, detent, or snap fit. In many embodiments, the anchor body has a circular cross-section.

In some embodiments, the channel comprises a threaded region along at least a portion of an interior surface of the channel.

In many embodiments, the anchor body comprises a diameter within a range of about 3 mm to about 6.5 mm. In many embodiments, the anchor body comprises a length between the proximal end and the distal end within a range of about 10 mm to about 30 mm. In many embodiments, the insert body has a circular cross-section.

In many embodiments, the insert body comprises a diameter within a range of about 1.8 mm to about 4 mm. In many embodiments, the insert body comprises a length between the proximal end and the distal end within a range of about 4 mm to about 10 mm. In many embodiments, the insert further comprises a device coupler configured to couple the insert to a delivery device. In many embodiments, the device coupler comprises a cavity extending distally from the proximal end of the insert body. In many embodiments, the device coupler comprises a proximal protrusion extending proximally from the proximal end of the insert body.

In many embodiments, the first lateral side comprises a first suture groove extending parallel to the longitudinal axis of the anchor body from the first opening to the proximal end of the anchor body and wherein the second lateral side comprises a second suture groove extending parallel to the longitudinal axis of the anchor body from the second opening to the proximal end of the anchor body.

In many embodiments, the proximal end of the anchor body comprises a proximal taper which terminates the first suture groove distal to the proximal end of the anchor body. In many embodiments, the anchor body comprises an interruption which terminates the first suture groove proximal to the first opening. In many embodiments, the first suture groove comprises a proximal step which reduces a depth of the first suture groove at the proximal end of the anchor body.

In many embodiments, one or more bone engaging ridges may be disposed on an outer surface of the anchor body. In many embodiments, the one or more bone engaging ridges comprise a bump, a ridge, a rib, a thread, a scale, an extension, a protrusion, or a projection. In many embodiments, at least one of the one or more bone engaging ridges is located distal of the first opening and the second opening. In many embodiments, the distal end of the anchor body comprises a distal tip. In many embodiments, the distal tip is pointed, conical, tapered, or blunt.

In many embodiments, the anchor comprises polyetheretherketone (PEEK), polylactic acid (PLA), or polyglycolic acid (PGA). In many embodiments, the insert comprises polyetheretherketone (PEEK), polylactic acid (PLA), or polyglycolic acid (PGA). In many embodiments, the system comprises a suture disposed through the suture passage. In many embodiments, at least two sutures are disposed through the suture passage.

In one or more embodiments, the components described herein may be part of a suture anchor system, or a suture anchor kit, the system or including a delivery device comprising a driver configured to couple to a device coupler of the insert; a bone drill, a drill guide for positioning a drill bit of the bone drill, wherein the bone drill is configured to bottom out on the drill guide once it has reached a predetermined depth. In some embodiments, the drill guide may comprise a partially enclosed circular guide at a distal end, or a fully enclosed circular guide at a distal end. In some embodiments, the suture anchor in the suture anchor kit may have a channel which is threaded along at least a portion of its length, wherein the insert body is threaded along at least a portion of its length, and the insertion tool is configured to thread the insert body into the channel by rotating a handle on the insertion tool. In many embodiments, the delivery device may further comprise an inner shaft and wherein the driver is translatably or rotationally disposed within the inner shaft, possibly in response to rotation of a handle on the delivery device. In some embodiments, the suture anchor kit further comprises a suture. In some embodiments, the suture comprises: a #2 UHMWPE braided suture; a suture tape; a flat braid configuration; a round to flat braid configuration; a 2.3 mm round to flat tape suture; a tapered tail; a nonabsorbable material, polyester, an absorbable material, or polyglactin (PGLA).

In some embodiments, the suture anchor system may further comprise a surgical broach tool, the broach tool comprising a proximal end, a distal end, a longitudinal axis, a shaft running along the longitudinal axis, at least two fins projecting outward from the shaft, and a plurality of bone engaging ridges on an exterior surface of the fins. In some embodiments, the fins are tapered, being longest at the proximal end of the broach and shortest at the distal end of the broach. In some embodiments, there are two fins. In some embodiments, the fins project outward from the shaft in opposite directions. In some embodiments, the angle between the fins is approximately 180 degrees. In some embodiments, the angle between the fins projecting outward from the shaft is less than 180 degrees. In some embodiments, the angle between the fins projecting outward from the shaft is approximately 90 degrees. In some embodiments, the shaft is partially hollow and configured to attach to a handling tool. In some embodiments, the fins are longer than they are wide. In some embodiments, the one or more fins of the broach tool are configured to align with the first and second lateral side of the anchor body. In some embodiments, the one or more fins of the broach tool are configured to align with the openings of the suture passage on the anchor body. In some embodiments, the broach tool comprises a shaft having a longitudinal axis and one or more fins projecting outward from the shaft. In some embodiments, the broach tool comprises a plurality of bone engaging ridges on an exterior surface of the one or more fins. In some embodiments, each fin of the one or more fins projects outward from the shaft with i) a first projection length located at a proximal portion of the fin, and ii) a second projection length located at a distal portion of the fin, wherein the first projection length is greater than the second projection length, and wherein the fin tapers from the first projection length to the second projection length.

Provided herein are methods of anchoring a tissue to bone. An exemplary method comprises a) positioning an anchor into a bone, the anchor comprising: an anchor body having a proximal end, a distal end, a longitudinal axis, a first lateral side extending between the proximal end and the distal end, and a second lateral side extending between the proximal end and the distal end, a suture passage comprising a proximal surface and a distal surface and extending through the anchor body from a first opening in the first lateral side to a second opening in the second lateral side, a channel extending along the longitudinal axis of the anchor body from a proximal opening in the proximal end of the anchor body to a distal opening in the proximal surface of the suture passage, wherein the channel does not extend past the distal surface of the suture passage, and a suture disposed through the suture passage; b) passing the suture through or around a tissue to be repaired; c) tensioning the suture to secure the tissue to the bone; d) longitudinally translating the insert within the channel towards the distal surface of the suture passage; and e) compressing the suture between the distal end of the insert and the distal surface of the suture passage, thereby locking the suture in the suture passage.

In many embodiments, the distal surface of the suture passage is v-shaped and has a first lateral plane extending from the first opening towards a central normal plane and a second lateral plane extending from the second opening towards the central normal plane, the central normal plane being substantially perpendicular to the longitudinal axis of the anchor body. In many embodiments, the distal surface of the suture passage is substantially flat and substantially perpendicular to the longitudinal axis of the anchor body.

In many embodiments, at least a portion of the distal surface of the suture passage comprises a convex curvature extending proximally towards the distal opening of the channel. In many embodiments, a proximal portion of the convex curvature extends into the distal opening of the channel. In many embodiments, the convex curvature spans the entire distal surface.

In many embodiments, the distal end of the insert is shaped to correspond to the distal surface of the suture passage. In many embodiments, the distal end of the insert is rounded. In many embodiments, the distal end of the insert has a curved outer boundary. In many embodiments, the distal end of the insert is v-shaped. In many embodiments, the distal end of the insert has a dimpled distal surface. In many embodiments, the first opening or the second opening has a polygonal shape.

In many embodiments, at least a portion of an inner surface of the channel comprises threading, wherein at least a portion of an outer surface of the insert body comprises correspondingly-shaped threading, and wherein longitudinally translating the insert comprises rotating the insert relative to the channel. In many embodiments, the insert comprises a device coupler for coupling the insert to a delivery device with the device coupler. In many embodiments, the device coupler comprises a cavity extending distally from the proximal end of the insert body. In many embodiments, the device coupler comprises a proximal protrusion extending proximally from the proximal end of the insert body.

In many embodiments, the method comprises retaining the anchor in the bone with one or more bone engaging ridges disposed on an outer surface of the anchor body. In many embodiments, the one or more bone engaging ridges comprise a bump, a ridge, a rib, a thread, a scale, an extension, a protrusion, or a projection. In many embodiments, positioning the suture anchor comprises driving the suture anchor into the bone without drilling a hole. In many embodiments, positioning the suture anchor comprises inserting the suture anchor into a pre-drilled hole in the bone. In many embodiments, the method comprises drilling the hole in the bone prior to positioning the suture anchor therein. In many embodiments, the method comprises locking the insert in the channel after compressing the suture.

Aspects disclosed herein further provide a method of repairing ligaments in the ankle in a subject, the method comprising: a. inserting a first suture anchor into a first bone, wherein the first suture anchor is the suture anchor system of claim 1 and comprises a suture; b. passing the suture through a first ligament; c. threading a second suture anchor with the suture, wherein the second suture anchor is the suture anchor system of claim 1; d. inserting the second suture anchor into a second bone; e. tensioning the suture between the first suture anchor and the second suture anchor; f. threading a third suture anchor with the suture, wherein the third suture anchor is the suture anchor system of claim 1; g. inserting the third suture anchor into a third bone; h. tensioning the suture between the second suture anchor and the third suture anchor; and i. trimming the remaining suture. In some embodiments, the first bone is a lateral process. In some embodiments, the second bone is a fibula. In some embodiments, the third bone is a calcaneus. In some embodiments, the first ligament is the anterior talofibular ligament. In some embodiments, the method further comprises passing the suture through a second ligament following step f. In some embodiments, the second ligament is the calcaneofibular ligament. In some embodiments, the method further comprises drilling a hole in a distal end of the fibula at approximately a 90 degree angle relative to the longitudinal axis of the second suture anchor; and passing the suture through the hole in the distal end of the fibula. In some embodiments, the suture passes through the fibula and exits at a direction approximately 90 degrees relative to where the suture entered the fibula. In some embodiments, the first suture anchor is inserted approximately 2 cm from the lateral process. In some embodiments, the second suture anchor is inserted 1 cm proximal to the tip of the distal fibula. In some embodiments, the ligament repair is a Brostrom repair. In some embodiments, steps c and d are performed prior to steps a and b. In some embodiments, steps c and d are performed prior to steps a and b, and steps f and g are performed prior to steps a and b.

These and other embodiments are described in further detail in the following description related to the appended drawing figures.

BRIEF DESCRIPTION OF THE DRAWINGS

FIG. 2I shows a front and a top view of a surgical broach, and descriptions of broach dimensions in certain embodiments.

FIG. 6 shows a process flow diagram illustrating surgical methods for use with suture anchors of some embodiments.

FIG. 9 shows exploded views of the suture anchor system of some embodiments with a suture in the suture passage.

DETAILED DESCRIPTION

Figure 1A:
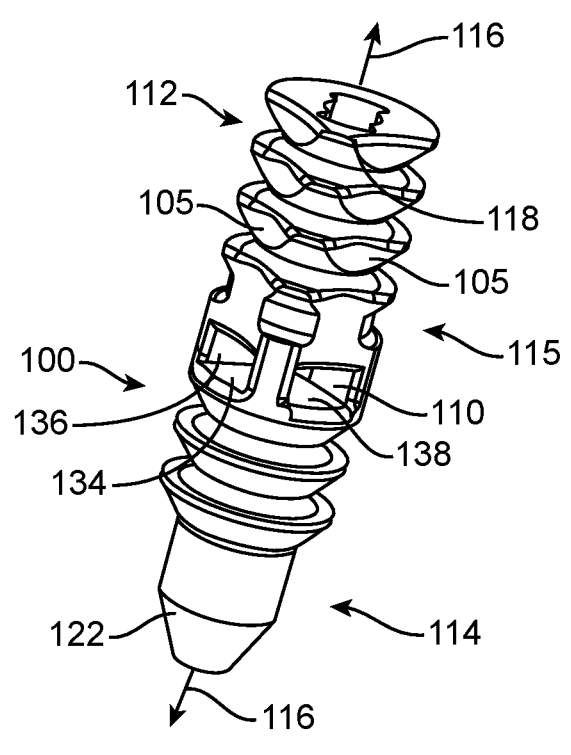
FIG. 1A shows a perspective view of a suture anchor, in accordance with some embodiments.

Specific embodiments of the disclosed device and method of use will now be described with reference to the drawings. Nothing in this detailed description is intended to imply that any particular component, feature, or step is essential to the invention.

It is appreciated by the inventors that it is desirable to design a suture anchor system which will increase the lifespan of the suture and suture anchor system by limiting the surface interactions between the suture and the suture anchor. Embodiments of improved suture anchors that are discussed herein have been designed to preserve integrity of the suture when in use. Some embodiments may comprise smooth or rounded edges on one or more anchor surfaces, and centrally located passages which reduce displacement between the end of a suture and tissues attached thereto, may reduce friction placed on the suture by the anchor, may provide increased anchor pull out strength, and may require less preparation of bone surface by other components of a suture anchor system (e.g., a surgical broach). It is desirable to provide improved suture anchors which are designed to preserve integrity of the suture when in use.

It is also desirable to provide improved knotless suture anchor devices and methods that overcome some of the challenges of existing devices. For example, it is desirable to provide a knotless suture anchor device that locks into place on the suture material while maintaining the integrity of the suture material. Additionally, it is desirable to provide a knotless suture anchor that may be used to secure soft tissue that is engaged by the suture material.

For example, one or more embodiments may utilize an improved suture anchor having a centrally located suture passage at least ⅓ of the way up the anchor body, which may reduce the length of the suture and the displacement from the bone tissue it is anchored to. Additional embodiments may include a plurality of rounded recesses on an exterior surface of a segmented anchor body along the segments positioned between the suture passage and a proximal end of the anchor body; the plurality of rounded recesses defining a suture channel. There may be a rounded edge along each of the rounded recesses. The centrally located suture passage and suture groove defined by rounded recesses with rounded edges may reduce the friction placed upon the suture by the suture anchor, allowing the suture to contact the suture anchor at more natural angles, placing less pressure on the suture as compared to sharp angles, reducing friction placed on the suture by the suture anchor, thus extending the life of the suture, and improving patient outcomes. In some embodiments, the suture passage may be approximately in the center of the anchor body.

In another aspect, it is desirable to design a suture anchor system with increased resistance from pulling out of the bone by increasing surface interactions between the suture anchor and the bone, possibly by improving preparation of the bone. For instance, there may be incorrect preparation of bone tissue for insertion of a suture anchor in the absence of cavity enlargement by removal or compression of cancellous bone tissue. In addition, such cavities may also be too large as a result of excess removal or compression of cancellous bone tissue. Accordingly, surgical broaches which are configured to remove or compress bone tissue to the proper size for a given suture anchor may help to facilitate improved patient outcomes.

For example, improved suture anchor systems of present embodiments may also include a surgical broach tool. The surgical broach may have a proximal end, a distal end, a longitudinal axis, a shaft running along the longitudinal axis, at least two fins projecting outward from the shaft, and a plurality of bone engaging ridges on an exterior surface of the fins. The fins may be tapered, being longest at the proximal end of the broach and shortest at the distal end of the broach. There may be two such fins. The fins may project outward from the shaft in opposite directions, and the angle between the fins may be approximately 180 degrees. Alternatively, the angle between the fins projecting outward from the shaft may be less than 180 degrees, and may be approximately 90 degrees. The shaft of the surgical broach may be partially hollow and configured to attach to the exterior surface of the anchor body between the suture passage and the proximal end of the anchor body.

The surgical broach may be used to compact the cancellous bone tissue and cortical bone tissue along the length of the suture groove in order to provide additional space for the sutures, improving the ability of a suture to slide within the suture groove, and a surgeon's ability to tension the suture following anchor insertion. The surgical broach may result in smooth or rounded edges or corners along the cortical bone surface where the suture contacts the bone, allowing the suture to pull the suture anchor at an angle other than 90 degrees, increasing the pull out strength of the suture anchor system, as well as extending the life of the suture anchor system by reducing friction placed on the suture by the bone. In addition, the compaction of the bone tissue surrounding the suture groove and suture may also allow the bone to heal around all sides of the suture or suture tape.

Other embodiments may utilize locking inserts that are used to engage a suture or sutures are configured to spread pressure across a large area while still maintaining sufficient compression of the suture to lock it in place. By spreading pressure across a large area, an insert provides less focused pressure to the suture when compared to an insert that pinches a suture at severe angles against one or more edges of a suture anchor.

It is further appreciated by the inventors that prior art suture anchors are inadequate for facilitating soft tissue repair around the ankle because the high stress placed on the sutures due to the biomechanics of the fibular ligaments which are often the subject of surgical repair. For instance, most suture anchors do not allow sutures to exit the suture anchor in a direction that is 90 degrees (or approximately 90 degrees) relative to the direction in which it entered the suture anchor, or through a bone tunnel (e.g., the fibular bone tunnel), as may be desirable when repairing the ligaments of the ankle, such as the fibular ligaments.

Accordingly, one or more embodiments of suture anchors of and surgical methods of use for facilitating repair of soft tissue repair of the ankle are disclosed herein. Suture anchors of one or more embodiments may comprise a suture passage with first and second openings orientated in a first and second lateral surface of an anchor body that are orientated approximately 90 degrees relative to one another, may comprise a suture channel extending along the longitudinal axis of the anchor body from a proximal opening in the proximal end of the anchor body to a distal opening in the suture passage, and may allow for suture to be threaded through the suture anchor at the top of the anchor. Such embodiments may allow the suture to run outward from the anchor at an orientation of 90 degrees relative to its initial angle of entry, and may be uniquely optimized for facilitating repair of soft tissues in the ankle.

For instance, disclosed are surgical methods which utilize a single suture as a continuous thread for repair or support of a ligament in the angle, passing through two or more suture anchors. The suture anchors may permit such use of a single suture as a continuous thread by permitting the single suture to be tensioned at each suture anchor, and pass through each suture anchor at approximately 90 degree angles, permitting the suture anchor to enter in a first direction, and exit in a second direction. Such surgical methods using suture anchor systems of present embodiments may be useful for facilitating improved Brostrom repair procedures, or other surgical procedures repairing ligaments in the ankle.

Suture anchors of one or more embodiments may represent a significant improvement in improving suture anchor systems by improving suture longevity or increasing anchor pull out resistance, including, for example, in the ankle.

The embodiments described herein address at least some of these challenges and benefits.

Devices and methods as disclosed herein provide a suture anchor that may be used to fixate soft tissue to bone. Suture anchors as described herein may be used for surgeries such as labral repair, muscle repair, tendon repair, and ligament repair, in addition to other examples of surgery, including, for example, Brostrom repair. In some embodiments, a method of performing an improved Brostrom repair with suture anchor systems of present embodiments is disclosed. In some embodiments, suture anchors as provided herein may be used in surgery by first drilling a pilot hole into a bone of a patient; inserting the suture anchor into the bone; passing suture material from the suture anchor around soft tissue; providing tension to the suture material to hold the tissue again a corresponding bone; and locking the suture into place by compressing an insertion member to engage the suture material while preserving the integrity of the suture material. In some embodiments, suture anchors as provided herein may be used in surgery by first drilling a pilot hole into a bone of a patient; preparing the bone using the broach tool by inserting the broach into the pilot hole, and malleating the broach until the wings are just below the surface of the cortical bone, inserting the suture anchor into the bone; passing suture material from the suture anchor around soft tissue; providing tension to the suture material to hold the tissue again a corresponding bone; and locking the suture into place by compressing an insertion member to engage the suture material while preserving the integrity of the suture material.

Figure 1B:
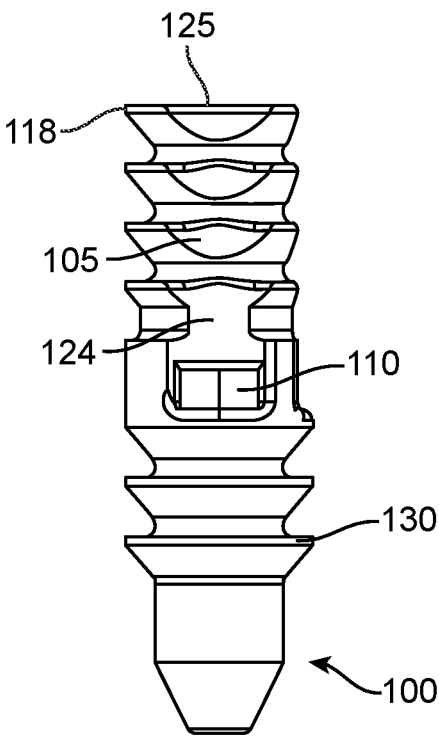
FIG. 1B shows a front view of a suture anchor, in accordance with some embodiments.
Figure 1C:
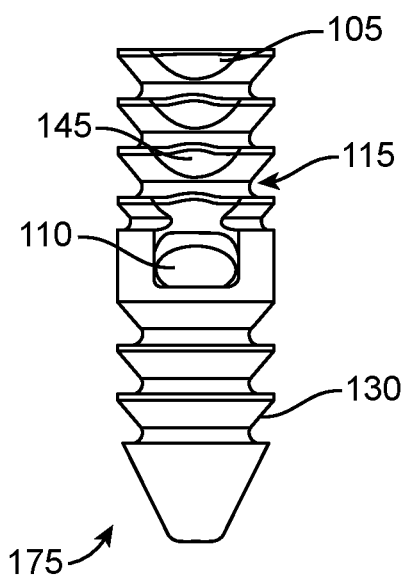
FIG. 1C shows a side view of a suture anchor, in accordance with some embodiments.
Figure 1D:
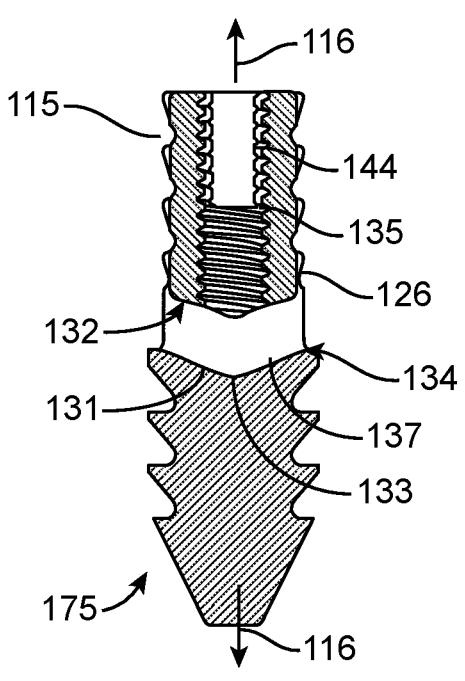
FIG. 1D shows a cross sectional view of a suture anchor, in accordance with some embodiments.
Figures 1E, 1F:
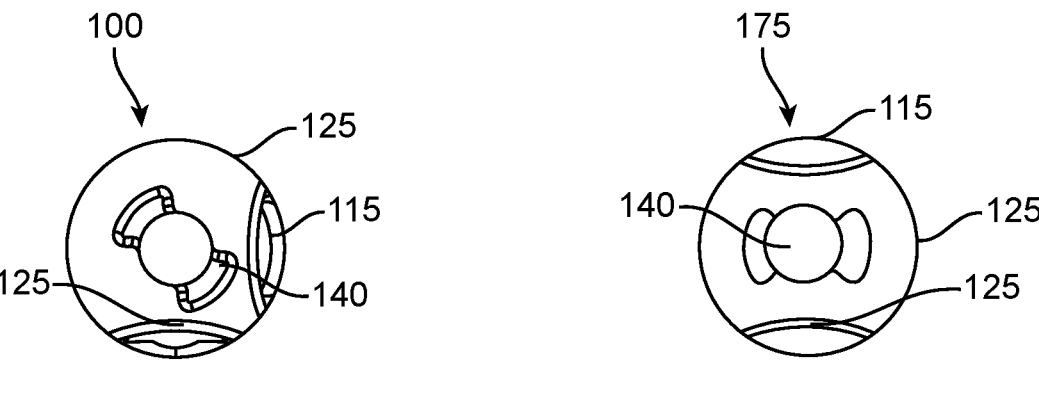
FIG. 1E shows a top view of a suture anchor, in accordance with some embodiments.
FIG. 1F shows a top view of a suture anchor, in accordance with some embodiments.

FIG. 1A shows a perspective view of a suture anchor 100. FIG. 1B shows a front view of the suture anchor 100. FIG. 1F shows a top view of the suture anchor 100. The suture anchor 100 may comprise an anchor body 115 having a proximal end 112, a distal end 114, a first lateral side 124 extending between the proximal end 112 and the distal end 114, and a 126 second lateral side extending between the proximal end 112 and the distal end 114. The second lateral side 126 may be positioned opposite laterally of the first lateral side 124, as illustrated in FIG. 1C, 1D, or 1F. For example, the angle between the first lateral side 124 and the second lateral side 126 may be approximately 180 degrees. In one or more embodiments, the second lateral side 126 may be positioned laterally adjacent to the first lateral side 124, as illustrated in FIGS. 1A, 1B, and 1E. For example, the angle between the first lateral side 124 and the second lateral side 126 may be approximately 90 degrees, or less than 90 degrees, for example, approximately 60 degrees, or approximately 30 degrees.

In some embodiments, the first lateral side and the second lateral side are positioned adjacent to one another. In some embodiments, an angle between the first lateral side and the second lateral side is 90 degrees. In some embodiments, the first lateral side and the second lateral side are positioned opposite one another. In some embodiments, an angle between the first lateral side and the second lateral side is 180 degrees.

In some embodiments, a first opening 136 is disposed in the first lateral side 124. A suture passage 110 extends through the anchor body 115 from the first opening 136 to a second opening 138 in the second lateral side. In some embodiments, the suture passage is configured to receive a suture (as described herein). In some embodiments, a suture groove 145 runs parallel to the longitudinal axis 116 of the anchor body 115 and extends from the first opening 136 to the proximal end 112. In some embodiments, a second suture groove runs parallel to the longitudinal axis 116 of the anchor body 115 and extends from the second opening 138 to the proximal end 112. In some embodiments, the distal end 114 comprises a distal tip 122.

In some embodiments, one or more external retention features 118 are disposed on an outer surface of the anchor body 115 to enhance friction or to mechanically enhance retention of the anchor 100 within the bone. In many embodiments, the one or more external retention feature comprises a bump, a ridge, a rib, a thread, a scale, an extension, a protrusion, or a projection, a barb, a hook, a spike, or the like, or any combination thereof. In many embodiments, at least one of the one or more external retention features is located distal of the first opening and the second opening. In one or more embodiments, the one or more external retention features may be bone engaging ridges. In some embodiments, the one or more external retention features are angled relative to a lateral axis of the anchor body, wherein the lateral axis is perpendicular to the longitudinal axis 116. In one or more embodiments, the one or more external retention features are angled proximally, thereby providing an increased pull-out strength (e.g., force required to pull out anchor body) as compared to having the external retention features disposed parallel with the lateral axis or angled distally compared with the lateral axis.

In some embodiments, the suture groove 145 is recessed relative to the one or more external retention features 118 to help ensure that a suture disposed therealong does not deviate its positioning from the suture groove. In some embodiments, the suture groove helps ensure a suture disposed therealong does protrude outward past the external retention features external retention feature(s) 118 to contact the bone. In some embodiments, the suture groove helps to reduce the amount of suture in contact with bone, or to reduce the pressure placed on the suture by the bone. In some embodiments, each suture groove is defined by a plurality of recesses 105 located external retention features (as described herein), and positioned between the suture passage and the proximal end of the anchor body. In some embodiments, the recesses 105 are rounded.

By providing sufficient space to avoid the suture contacting bone, the suture groove may permit sliding of the suture within the suture groove 145 (and suture passage 110, and other grooves described herein) and also enable adjustment of suture tension after the anchor 100 has been positioned in the bone but before the suture has been locked within the suture passage 110, further described below. The one or more external retention features 118 may further comprise a smooth surface to blunt the portion of the external retention feature(s) 118 directly adjacent to the suture to prevent damage to the suture. In some embodiments, the external retention features 118 may further comprise a smooth or curved edge adjacent to the suture groove 145 to blunt the portion of the external retention feature(s) 118 directly adjacent to the suture to prevent damage to the suture which may otherwise occur in at least some instances when the external retention feature(s) 118 have sharp edges adjacent the suture. In some embodiments, the smooth or curved edge adjacent to the suture groove 145 may be rounded. In some embodiments, at least one of the one or more external retention features 118 may be disposed distal to the opening (s) (e.g., first opening 136 and/or second opening 138) to the suture passage 110.

In addition, the recesses 105, which define the suture groove 145, may further comprise a smooth or curved edge 125 along the perimeter of the rounded recesses 105 where they contact a suture in the suture channel. In some embodiments, smooth or curved edge 125 may further comprise a rounded edge. The curved edges 125 may further permit may permit sliding of the suture within the suture groove 145 and adjustment of suture tension after the anchor 100 has been positioned in the bone but before the suture has been locked within the suture passage 110, further described below. The curved edges 125 may serve to provide a larger surface area which contacts the suture at less sharp angle than if the edges were flat or sharp, e.g., 90-degree angles. This may place less pressure upon the suture and may reduce friction between the suture and the suture anchor, reducing wear on the suture, and the risk of suture failure. Additionally, the curved edge 125 in the uppermost rounded recess at the proximal end of the suture anchor, may also permit the suture to pull on the suture anchor, and contact the bone, at a more natural angle (e.g., other than 90 degrees) then if the edges were sharp (see FIG. 1E/F). In placing tension on the suture anchor at an angle other than 90 degrees, the pull out strength of the suture can be improved, and the overall strength and longevity of the suture anchor system can be improved, possibly allowing a surgeon to utilize a smaller diameter suture anchor than would otherwise be possible. In addition, contacting the bone at a more natural angle also allows for better bone engagement, further optimizing the surgeon's ability to tension the suture, and further improving pull out strength. In providing rounded recesses 105 with curved edges 125 that define the suture groove 145, high pressure and high friction due to movement of the suture over what may otherwise be sharp edges, or flat edges with sharp angles, of the suture channel can be reduced, and patient outcomes can be significantly improved by providing a suture anchor system which carries a significantly reduced rate of suture failure.

In addition, the curved edges 125 may serve to provide a larger surface area contacting the suture tape, which also permits a larger sized suture or suture tape to be used, for example a suture tape having a flat or wide configuration, or multiple sutures fed through the anchor and resting in the suture groove. For example, in some embodiments, a suture tape having a width from about 0.5 mm to about 3.5 mm is configured to pass through a suture passage and suture groove from an embodiment of a suture anchor body described herein. In some embodiments, the suture tape used with an anchor body described herein has a width of from about 1.5 mm to about 3.0 mm, about 2.25 mm to about 2.75 mm, or about 2.5 mm. In some embodiments, such suture tapes having a width comprise a flat surface. In some embodiments, the curved edges 125 may permit the suture tape to sit better in the suture groove, for example, via a larger surface area that contacts the suture. In some embodiments, the curved edges 125 may permit for some lateral movement within the suture groove so as to reduce the stress and friction placed upon the suture.

Figure 1G:
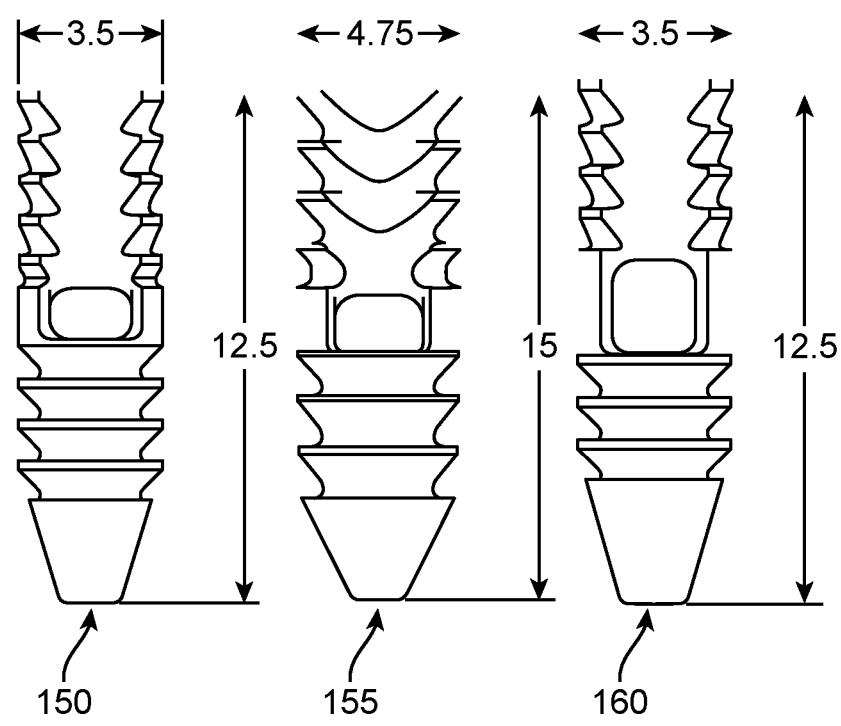
FIG. 1G. shows multiple suture anchors, in accordance with some embodiments.

The one or more external retention features 118 may comprise bumps, ridges, ribs, threads, scales, extensions, protrusions, projections, bone engaging ridges, or the like, or any combination thereof. FIG. 1G shows additional embodiments of suture anchors 150/155/160 comprising one or more of these features.

The suture passage 110 may be located anywhere along the suture anchor 100/175 body between the proximal end and the distal end of the anchor body. In some embodiments, the suture passage is located at least about 33%, 40%, 50%, 60%, 70%, or 80% of an anchor body length from the distal end. In some embodiments, the suture passage 110 may be centrally located along the suture anchor 100/175, and may be approximately halfway between the proximal end and the distal end of the anchor body. In some embodiments, the suture passage is located proximal to at least two external retention features 118, which are thereby located between the suture passage and the distal end of the anchor body. In some embodiments, at least one external retention feature is located proximal to the suture passage, which is thereby located between the suture passage and the proximal end of the anchor body. Accordingly, in some embodiments, the length of the suture required for a procedure depends on the location of a suture passage on the anchor body and the displacement from the bone tissue it is anchored to.

In some embodiments, the suture passage is located at least ⅓ of the way up the anchor body measured from the distal end of the anchor body. In some embodiments, the suture passage is approximately ⅔ of the way up the anchor body measured from the distal end of the anchor body.

In some embodiments, a benefit of the centrally located suture passage may include increasing the pull-out strength of the suture anchor system. By having a suture passage which is centrally positioned in the anchor body, it permits there to be additional external retention features on the anchor body below the suture passage, for example, between the suture passage and the distal end of the suture anchor. The additional external retention features, for example, bone engaging ridges, provide increased surface interactions between the suture anchor and the cancellous bone, increasing the pull out strength of the suture anchor system by 5%, 10%, 15%, 20%, 25%, or 30%. In some embodiments, the location of the suture passage along the anchor body permits optimization of the anchor body pull-out strength (e.g., force required to pullout an anchor body from a bone hole). For example, a more proximally located suture passage (for e.g., 33%, 40%, 50%, 60%, 70%, or 80% of an anchor body length from the distal end), permits for additional external retention features located distal to the suture passage to be included with anchor body, wherein such distally located external retention features may have increased surface area contact with a bone hole considering there is no need to define a suture groove (as compared to external retention features located proximal to the suture passage). Accordingly, in some embodiments, the length of the anchor body can be reduced due to the increased pullout strength achieved with an anchor having a suture passage located in a more proximal location (as described herein).

In some embodiments, the location of the suture passage in combination with the suture groove 145 defined by rounded recesses 105 with curved edges 125 may further reduce the friction placed upon the suture by the suture anchor as compared to a distally located suture passage. These features may allow the suture to contact the suture anchor at more natural angles, placing less pressure on the suture as compared to sharp angles, reducing friction placed on the suture by the suture anchor, thus extending the life of the suture, and improving patient outcomes.

In addition, the location of the suture passage may be further desirable as it may provide easier access to the suture passage, be easier for a surgeon to manipulate and tension a suture which is passing through a more proximally located suture passage 110, as compared to a distally located suture passage. The position of the suture passage may also enable better suture tape trajectory in reducing the distance the suture travels into the bone, and the angle at which it contacts the bone in traveling along the anchor and to the connected soft tissues. This may enable the suture to pull on the connected soft tissues in a more anatomical direction (e.g., aligned with the natural direction the ligament pulls) when compared to a distally located suture passage. In some embodiments, this may also result in reduced stress placed on the bone corners, and reduced loosing of the suture or suture tape, and overall loosening of the suture anchor system, if the bone corners erode or decay.

In some embodiments, the suture anchor system may comprise suture anchors with suture passages having different orientations. For example, there may be a suture anchor 100 with a suture passage 100 having windows which define the passage orientated at a 90 degree angle relative to one another; or there may be a suture anchor 175 with a suture passage 100 having windows which define the passage orientated at a 180 degree angle relative to one another. In other embodiments, the suture passage may be defined by windows at 30 degrees, 45 degrees, 60 degrees, or another measurement. In providing a suture anchor system with suture anchors having suture passages of varying orientation along the anchor body, it is possible to choose a particular suture anchor based on anatomy and the particular tissue being repaired, and may permit a surgeon to construct a suture anchor system that allows the tissue being repaired, for example, ligaments, to be tethered to sutures which sit at a more natural angle relative to the original position of the ligaments being repaired, and which will pull on the ligaments being repaired at a more natural angle relative to the original position of the ligaments being repaired when compared to suture anchors systems only having a single orientation. In a non-limiting example, considering the case of the improved Brostrom repair procedure described below, utilizing a suture anchor inserted into the distal fibula with a suture passage orientated at a 90-degree angle may permit the suture to pull on the anterior talofibular ligament at a natural angle when tethered to the calcaneofibular ligament which connects to the fibula approximately at a 90-angle relative to the anterior talofibular ligament.

Referring to FIGS. 1A-1F, the distal tip 122 of the suture anchor 100/175 may be conical, pointed, tapered, blunt, or the like as will be understood by one of ordinary skill in the art based on the teachings herein.

In some embodiments, the first opening 136 (and second opening 138) may have a polygonal cross-section. The suture passage 110 may also have a polygonal cross-section. In some embodiments, the first opening 136 (and second opening 138) may have a square cross-section. The suture passage 110 may also have a square cross-section. In some embodiments, the first opening 136 (and second opening 138) may have a rectangular cross-section. The suture passage 110 may also have a rectangular cross-section. In some embodiments, the polygonal cross-section may be triangular, quadrilateral (e.g., square or rectangular), pentagonal, hexagonal, octagonal, nonagonal, decagonal, or any other cross-section desired by one of ordinary skill in the art.

In some embodiments, the first opening 136 (and second opening 138) may have a cross-section that is asymmetrical, circular, or curved.

In some embodiments, the first opening 136 (and second opening 138) may have a width within a range of about 1 mm to about 3 mm, such as about 1.2 mm to about 2.5 mm. For example, the width may be within a range of about 1.5 mm to about 2 mm.

In some embodiments, the first opening 136 (and second opening 138) may have a height within a range of about 1 mm to about 4 mm, such as about 1.2 mm to about 2.5 mm. For example, the height may be within a range of about 1.5 mm to about 2 mm.

In some embodiments, the suture passage 110 may have a width within a range of about 1 mm to about 3 mm, such as about 1.2 mm to about 2.5 mm. For example, the width may be within a range of about 1.5 mm to about 2 mm.

In some embodiments, the suture passage 110 may have a height within a range of about 1 mm to about 3 mm, such as about 1.2 mm to about 2.5 mm. For example, the height may be within a range of about 1.5 mm to about 2 mm.

In some embodiments, the anchor body 115 may have a length between the proximal end 112 and the distal end 114 within a range of about 10 mm to about 30 mm, such as about 12 mm to about 25 mm. For example, the anchor body 115 may be about 10 mm, 12.5 mm, 15 mm, 17.5 mm, 20 mm, or 21 mm long. The size and length of the anchor body may be selected based upon the intended location of implantation and surgical produce for which it is used.

In some embodiments, the anchor body 115 has a circular cross-section as shown in FIGS. 1E-1F.

In some embodiments, the anchor body 115 has an outer diameter within a range of about 3 mm to about 6.5 mm, such as about 3.5 mm to about 6.5 mm. For example, the anchor body 115 may have an outer diameter of about 3.5 mm, about 3.75 mm, about 4.5 mm, or about 5.5 mm.

In some embodiments, the anchor body 115 may comprise a radiolucent material, such as polyetheretherketone (PEEK). In some embodiments, the anchor body 115 comprises a biocomposite or bioabsorbable material, such as polylactic acid (PLLA). In some embodiments, the anchor body 115 comprises a biodegradable material, such as polyglycolic acid (PGA). In some embodiments, the anchor body 115 comprises a combination of materials. In some embodiments, one or more of the materials may be radiopaque. For example, the anchor body 115 may comprise radiopaque PEEK (non-translucent). The suture anchor 100 may comprise PEEK, biocompatible material. Similarly, the surgical broach 200 may also comprise PEEK, a biocompatible material.

The suture anchor 100 may comprise an insert 140 in either an unlocked configuration or a locked configuration. When in a locked configuration, the insert may compress the suture 310 within the suture passage 110, against the distal end of the suture passage. The suture passage 110 may a proximal surface 132 and a distal surface 134. The insert 140 may be disposed within a channel 144 extending along the longitudinal axis 116 of the anchor body 115 from a proximal opening to a distal opening in the proximal surface 132 of the suture passage 110. Longitudinal translation of the insert 140 within the channel 144 towards the distal surface 134 of the suture passage 110 from the unlocked configuration to the locked configuration compresses the suture 310 between the distal end of the insert 140 and the distal surface 134 of the suture passage 110 in order to secure the suture 310 in the suture passage 110 as described herein.

The distal surface 134 of the suture passage 110 may be v-shaped. The v-shaped distal surface 134 can comprise a first lateral plane 131 extending at an angle from the first opening 136 toward a central normal plane 133 and a second lateral plane 137 extending at an angle from the second opening 138 toward the central normal plane 133. The central normal plane 133 is substantially perpendicular to the longitudinal axis 116 of the anchor body 115. In some embodiments, there may be no central normal plane 133 and the first and second lateral planes 131, 137 come together at a point or curved junction. The v-shaped distal surface 134 provides a surface without sharp edges and therefore enables distribution of forces along a length of the suture 310 instead of concentrated pressure points (which occur with sharp edges) when the insert 140 is in the locked configuration. In at least some instances, spreading the forces over a length of the suture will benefit suture integrity, enabling better locking, less strain on the suture, and reduced risk to patients that the suture will fail after implantation.

In some embodiments, three or more points of capture of the suture 310 exist within the suture passage 110. For example, when the distal surface 134 of the suture passage 110 is v-shaped, the suture 310 is captured by at least a first capture point, a second capture point, and a third capture point. The first capture point may be between the suture 310 and a first lateral side of the distal end 156 of the insert 140. The second capture point may be between the suture 310 and a second lateral side of the distal end 156 of the insert 140. The third capture point may be between the distal end 156 of the insert 140 and the distal surface 134 of the suture passage 110. In some embodiments, for example, when the suture 310 does not contact the central normal plane 133 of the distal surface 134 of the suture passage 110, the suture 310 may contact one or more of the first lateral plane 131 or the second lateral plane 137 at one or more capture points. In at least some instances, providing three or more capture points will increase the pull-out force necessary to dislodge the suture 310 and provide better securing of the suture 310 after implantation.

The first lateral plane 131 may extend from the first opening 136 towards the central normal plane 133 at an angle relative to the longitudinal axis 40 within a range of about 30° to about 80°.

The second lateral plane 137 may extend from the second opening 138 towards the central normal plane 133 at an angle relative to the longitudinal axis 40 within a range of about 30° to about 80°.

In some embodiments, the channel 144 opens into the suture passage 110 and does not extend past the distal surface 134 of the suture passage 110. In some embodiments, for example as shown in FIG. 1D, the distal surface 134 comprises a pocket which extends the channel 144 distally beyond the distal surface 134 of the suture passage 110.

In some embodiments, at least a portion of an inner surface of the channel 144 comprises threading 135. In some embodiments, a portion of the inner surface of the channel 144 comprises threading 135 and a portion of the inner surface of the channel 144 (e.g., a proximal portion as shown) is not threaded. The insert 140 may comprise corresponding threading (e.g., threading shown in FIG. 7A)

In some embodiments, the inner surface of the channel 144 may not be threaded.

In some embodiments, one or both of the anchor body 115 or the insert 140 comprises a locking mechanism configured to lock the insert 140 in the channel 144. The locking mechanism optionally comprises a ratchet, a detent, a press fit, a snap fit, or the like as will be understood by one of ordinary skill in the art based on the teachings herein. In some embodiments, the threading 135 may act as a locking mechanism.

As will be understood by one of ordinary skill in the art based on the teachings herein, one or more sutures may be disposed within the suture passage 110 and suture grooves 145 of the anchors 10 described herein. For example, one, two, three, or four sutures may be disposed within the suture passage 110. In at least some instances, the use of two or more sutures may add strength and/or reduce the risk of suture failure compared to a single suture alone. The number of sutures may be selected based on the surgical method (e.g., the size of a rotator tear can determine the number of anchors and sutures used whereas a bicep tendon repair typically only has two tails (one suture) which wrap around the tendon), physiology, and/or surgeon preference. For example, a Bostrom repair may utilize one suture.

As will be understood by one of ordinary skill in the art based on the teachings herein, one or more sutures (or suture tapes) may be disposed within the suture passage 110 and suture groove(s) 145 of the anchors 10 described herein. For example, four or more sutures may be disposed within the suture passage 110. The four sutures may be disposed within the suture passage 110 such that two sutures lie on top of the other two sutures. For example, the second suture may be stacked above the first suture and the fourth suture may sit above the third suture. The two pairs of sutures may sit side by side within the suture passage 110. The stacked suture pairs can be locked between the distal surface 134 of the suture passage 110 and the distal end 156 of the insert 140 as described herein. The stacked suture pairs may substantially fill the suture passage 110. Even in the locked position, the stacked suture pairs may prevent the insert 140 from blocking the first and second openings of the suture passage 110 and/or from entering the suture passage 110 entirely. In some embodiments, each suture groove 145 may be at least two suture widths wide and at least one suture width deep.

In some embodiments, each suture groove may be at least one suture tape wide and at least one suture tape deep.

The insert 140 may comprise an insert 140 having a proximal end and a distal end. The insert 140 may be configured to translate longitudinally within a channel 144 of an anchor body between a proximal end of the anchor body and a distal surface of a suture passage. At least a portion of an outer surface of the insert 140 comprises threading shaped to correspond to threading 135 in the channel. Longitudinal translation of the insert 140 within the channel may occur when the insert 140 is rotated relative to the channel as described herein.

Figure 3A:
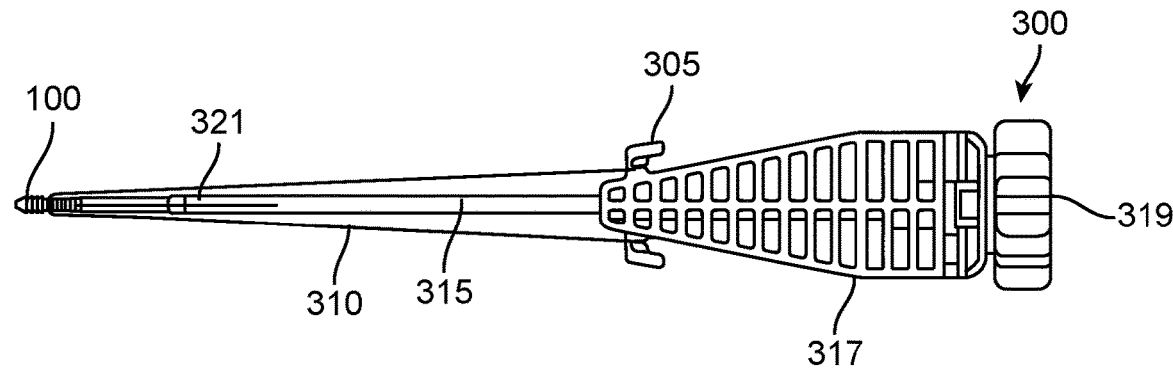
FIG. 3A shows a suture anchor placed within a delivery device, according to some embodiments.
Figure 3B:
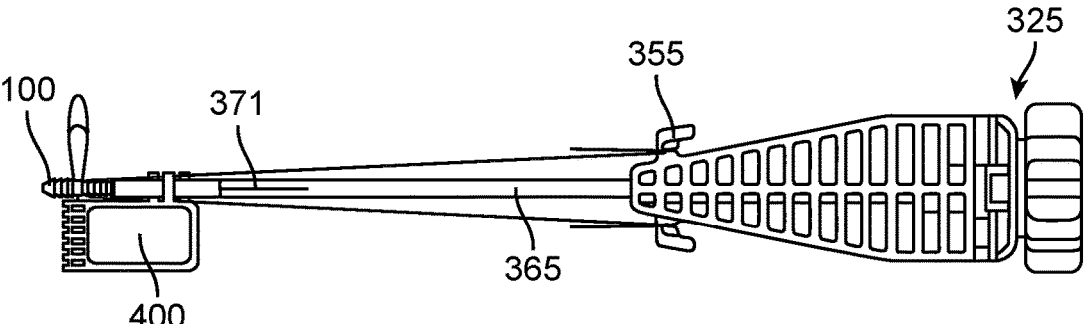
FIG. 3B shows a front view of suture anchor placed within another delivery device and attached to a suture threading tool, according to some embodiments.
Figure 3C:
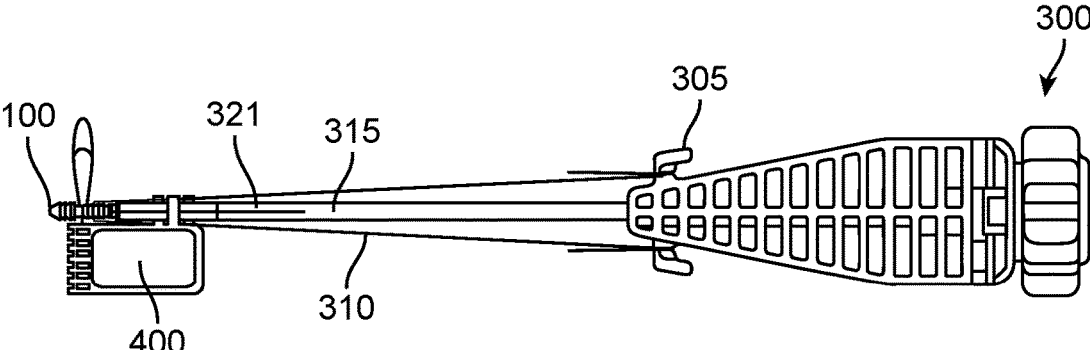
FIG. 3C shows a front view of suture anchor placed within a delivery device and attached to a suture threading tool, according to some embodiments.

In some embodiments, the insert 140 may comprise a device coupler configured to couple the insert 140 to a delivery device (e.g., delivery device 300 shown in FIGS. 3A-3C). The device coupler optionally comprises a cavity extending distally from the proximal end of the insert body.

The distal end of the insert is optionally rounded to avoid pressure points on the sutures. In some embodiments, the majority of the surface of the distal end 156 is planar with a curved outer boundary along the edges.

In some embodiments, the insert has a length between the proximal end and the distal end within a range of about 4 mm to about 10 mm.

In some embodiments, the insert has a curved or circular cross-section. In some embodiments, the insert 140 has a cross-section that has at least one edge (i.e., is not entirely curved). For example, in some embodiments, such as when screwing is not required for insertion, the insert 140 may have a triangular, quadrilateral (e.g., square or rectangular), pentagonal, hexagonal, octagonal, nonagonal, decagonal, asymmetrical, or any other cross-section desired by one of ordinary skill in the art.

In some embodiments, the insert 140 has an outer diameter within a range of about 1.8 mm to about 4 mm. For example, the insert 140 may have an outer diameter within a range of about 2 mm to about 3 mm.

In some embodiments, the insert 140 comprises a radiolucent material, such as polyetheretherketone (PEEK). In some embodiments, the insert 140 comprises a biocomposite or bioabsorbable material, such as polylactic acid (PLLA). In some embodiments, the insert 140 comprises a biodegradable material, such as polyglycolic acid (PGA). In some embodiments, the insert 140 comprises a combination of materials. In some embodiments, the insert 140 comprises the same material as the anchor body 115. In some embodiments, the insert 140 and the anchor body 115 comprise different materials.

In some embodiments, the insert's distal end 156 may be v-shaped to correspond to the V-shape of the distal surface 134 of the suture passage 110 of the anchor 100.

In some embodiments, the distal end 156 of the insert 140 is shaped to correspond to the distal surface 134 of the suture passage 110 of the anchor 100. For example, a bullet-shaped distal end 156 may correspond to a u-shaped distal surface 134 or a flat distal end 156 may correspond to a flat distal surface 134. Matching the shape of the distal end 156 of the insert 140 to the distal surface 134 of the suture passage 110 may help to distribute the pressure applied to the suture 310 by the insert 140 while still maintaining sufficient compression of the suture 310 to lock it in place when the insert 140 is in the locked configuration.

In some embodiments, the insert 140 may have dimpled surface. The dimpled surface may pinche the suture 310 against the distal surface 134 of the suture passage 110 at the outer edge of the insert 140 as opposed to the more central pinching of a rounded insert. In at least some instances, the dimple reduces the surface area of the distal end 156 of the insert 140 touching the suture 310 which may make the suture 310 less likely to slide when then the insert 140 is being rotated into the locked configuration.

It will be understood by one of ordinary skill in the art that any of the insert described herein may be used in conjunction with any of the anchor bodies described herein in order to achieve a desired distribution of pressure along the suture(s), a desired number and/or location of contact points with the suture(s), a desired amount of compression of the suture(s), or the like.

In some embodiments, the suture anchor system comprises an anchor 100 and an insert 140 disposed within a channel 144 of the anchor body 115. The anchor 100 may be substantially similar to any of the anchors described herein except that the inner surface of the channel does not comprise threading. The insert 140 may be substantially similar to any of the inserts described herein. The outer surface of the insert 140 may not comprise threading. The channel 144 and insert 140 are configured to longitudinally translate without requiring relative rotation therebetween. In some embodiments, the insert 140 is configured to be press-fit into the channel 144.

In some embodiments, the insert 140 may be substantially similar to any of the inserts described herein except that the coupler 58 comprises a proximal protrusion extending proximally from the proximal end of the insert 140.

In some embodiments, the distal surface 134 of the suture passage 110 is optionally substantially flat. In some embodiments, the flat distal surface 134 is substantially perpendicular to the longitudinal axis 116 of the anchor body 115. The flat distal surface 134 provides a surface without sharp edges and therefore enables distribution of forces along a length of the suture 310 instead of concentrated pressure points (which occur with sharp edges) when the insert 140 is in the locked configuration. In at least some instances, spreading the forces over a length of the suture will benefit suture integrity, enabling better locking, less strain on the suture, and reduced risk to patients that the suture will fail after implantation.

In some embodiments, the insert 140 is disposed within a channel 144 extending along the longitudinal axis 116 of the anchor body 115 from a proximal opening 42 to a distal opening 44 in the proximal surface 132 of the suture passage 110. Longitudinal translation of the insert 140 within the channel 144 towards the distal surface 134 of the suture passage 110 from the unlocked configuration to the locked configuration compresses the suture 310 between the distal end 156 of the insert 140 and the distal surface 134 of the suture passage 110 in order to secure the suture 310 in the suture passage 110 as described herein.

In some embodiments, the suture groove may be recessed relative to the one or more external retention features 118 to ensure that a suture tape disposed there along does not protrude outward past the external retention feature(s) 118 to contact the bone, when the anchor is inserted within the bone. Compared to a rounded or square suture, suture tape may have a thinner and wider profile, the shape of the groove 145 (and other grooves) and suture passage 110 may be adjusted to accommodate the different shape and size of the suture tape so the suture tape lies flat therein. For example, the suture groove 145 may have a width within a range of about 1 mm to about 3 mm, for example within a range of about 1.8 mm to about 2 mm. The suture passage 110 can be dimensioned to compress one or more suture tapes therein with the insert 140. The suture tape can have a rounded tail in order to facilitate its uses with the same instruments and procedures as traditional sutures.

In some embodiments, the anchor 100 may be substantially similar to any of the anchors described herein except that the distal tip 122 is blunt.

In some embodiments, there may be longitudinal translation of the insert 140 within the channel 144 towards the distal surface 134 of the suture passage 110 from the unlocked configuration to the locked configuration compressing the suture 310 between the distal end 156 of the insert 140 and the distal surface 134 of the suture passage 110 in order to secure the suture 310 in the suture passage 110 as described herein.

In some embodiments, the distal surface 134 of the suture passage 110 optionally comprises a convex curvature extending proximally towards the distal opening of the channel 144. In some embodiments, the convex curvature extends into the distal opening of the channel 144. In some embodiments, the convex curvature spans the entire distal surface 134 of the suture passage 110.

The convex curvature may provide a surface without sharp edges and therefore enables distribution of forces along a length of the suture 310 instead of concentrated pressure points (which occur with sharp edges) when the insert 140 is in the locked configuration. In at least some instances, spreading the forces over a length of the suture will benefit suture integrity, enabling better locking, less strain on the suture, and reduced risk to patients that the suture will fail after implantation.

In some embodiments, three or more points of capture of the suture 310 exist within the suture passage 110. For example, when the distal surface 134 of the suture passage 110 is convex, the suture 310 is captured by at least a first capture point, a second capture point, and a third capture point. The first capture point may be between the suture 310 and a first lateral side of the distal end 156 of the insert 140. The second capture point may be between the suture 310 and a second lateral side of the distal end 156 of the insert 140. The third capture point may be between the distal end 156 of the insert 140 and the distal surface 134 of the suture passage 110. In at least some instances, providing three or more capture points will increase the pull-out force necessary to dislodge the suture 310 and provide better securing of the suture 310 after implantation.

In some embodiments, the convex curvature can have an arc angle within a range of about 3.5° to about 15°. For example, the convex curvature can have an arc angle of about 5.75°.

As will be understood by one of ordinary skill in the art based on the teachings herein, one or more sutures may be disposed within the suture passage 110 and suture groove(s) 145 of the anchors 100 described herein. For example, one, two, three, or four sutures may be disposed within the suture passage 110. In at least some instances, the use of two or more sutures may add strength and/or reduce the risk of suture failure compared to a single suture alone. The number of sutures may be selected based on the surgical method (e.g., the size of a rotator tear can determine the number of anchors and sutures used whereas a bicep tendon repair typically only has two tails (one suture) which wrap around the tendon), physiology, and/or surgeon preference.

For example, four or more sutures may be disposed within the suture passage 110. The four sutures may be disposed within the suture passage 110 such that two sutures lie on top of the other two sutures. For example, the second suture may be stacked above the first suture 310 and the fourth suture may sit above the third suture. The two pairs of sutures may sit side by side within the suture passage 110. The stacked suture pairs can be locked between the distal surface 134 of the suture passage 110 and the distal end 156 of the insert 140 as described herein. The stacked suture pairs may substantially fill the suture passage 110. Even in the locked position, the stacked suture pairs may prevent the insert 140 from blocking the first and second openings of the suture passage 110 and/or from entering the suture passage 110 entirely. Each suture groove 145, 74 is at least two suture widths wide and at least one suture width deep.

In some embodiments, the insert 140 is disposed within a channel 144 extending along the longitudinal axis 116 of the anchor body 115 from a proximal opening to a distal opening in the proximal surface 132 of the suture passage 110. Longitudinal translation of the insert 140 within the channel 144 towards the distal surface 134 of the suture passage 110 from the unlocked configuration to the locked configuration compresses the suture 310 between the distal end 156 of the insert 140 and the distal surface 134 of the suture passage 110 in order to secure the suture 310 in the suture passage 110 as described herein. The distal surface 134 may optionally comprise a pocket which extends the channel 144 distally beyond the distal surface 134 of the suture passage 110. The pocket may provide a space into which the suture 310 can be wedged in order to lock the suture 310 therein. The edges of the distal surface 134 at the pocket 39 provide distinct points of force on the suture 310 to help secure it. The edges of the distal surface 134 at the pocket 39 may act as a first point of capture 79a and a second point of capture 79b. In some instances, it may be desirable to lock the suture 310 within a pocket to prevent suture movement. In other instances, it may be less than desirable to stress the suture 310 at distinct points instead of spreading the force along a longer section of the suture 310. Such stress may damage the integrity of the suture 310 and/or wear down the suture faster than if a suture was secured using a suture anchor system that applied stress more evenly across the suture, such as other systems described herein. The choice of distal surface 134 configuration may depend on the surgical method, physiology, and/or surgeon preference.

In some embodiments, the anchor 100 may be substantially similar to any of the anchors described herein except that one or both of the suture groove(s) 145 terminate at distal end of a proximal taper in the proximal end 112 of the anchor body 115. The proximal taper may extend proximally from suture groove(s) 145 and reduces the depth of the suture groove(s) 145 near the proximal end 112 of the anchor body 115 such that the suture groove(s) 145 terminate at a point distal to the proximal end 112, before reaching the proximal end 112 of the anchor body 115. The portion of the proximal end 112 corresponding to the respective suture groove 145 location tapers along proximal taper from the suture groove(s) 145 to the proximal surface of the anchor 100 such that the suture groove(s) 145 is not visible at the proximal surface when looking at a top view of the anchor 100. In at least some instances, by not extending the suture groove(s) 145 through the proximal end 112 of the anchor body 115, the proximal end 112 of the anchor body 115 will be more robust and stronger against suture forces than a proximal end 112 with grooves which extend through the proximal end 112 and can act as failure points (due to the reduced thickness and strength of materials thereat) when sufficient forces are applied thereto.

In some embodiments, the anchor 100 may be substantially similar to any of the anchors described herein except that one or both of the suture groove(s) 145 is intersected by or terminates at an interruption. The interruption is config-ured to reduce the depth of the suture groove(s) 145 at a pre-determined location. The interruption may be located anywhere along the length of the suture groove(s) 145 as desired. For example, the interruption may be a distal interruption which reduces the depth of the suture groove(s) 145 just above the openings to the suture passage 110 such that the suture groove(s) 145 terminate before reaching the suture passage 110. Stated another way, the suture groove(s) 145 may be proximally spaced from the suture passage 110 via an interruption. In at least some instances, the interruption adds thickness to the anchor body 115 in pre-determined strategic locations in order to make the anchor body 115 more robust against off-axis insertion forces than a full groove 145 with a minimum wall would be. For example, when an interruption is placed distally (e.g., at or near the openings) along each of the suture groove(s) 145, the interruption(s) may help prevent failure mode if accidentally hit off-axis when the suture passage 110 is just below the surface of the bone. It will be understood by one of ordinary skill in the art that the interruption(s) can be located any-where along the length of the anchor 100 where added wall thickness of the anchor body 115 may be beneficial. For example, locating the interruption at the top of the openings away from the cortical bone layer, may be less impactful to suture movement.

In some embodiments, the anchor 100 may be substantially similar to any of the anchors described herein except that one or both of the suture groove(s) 145 comprise a proximal step. The proximal step may reduce the depth of the groove(s) 145 at the proximal end 112 of the anchor 100. For example, the proximal step may reduce the depth of the groove(s) 145 by about 50% at the proximal end 112 of the anchor 100 compared to the remainder of the groove(s) 145 extending along the anchor body 115. In at least some instances, by decreasing the depth of the suture groove(s) 145 at the proximal end 112 of the anchor body 115, the proximal end 112 of the anchor body 115 will be more robust and stronger against suture forces than a proximal end 112 with deeper grooves which extend through the proximal end 112 and can act as failure points (due to the reduced thickness and strength of materials thereat) when sufficient forces are applied thereto.

FIGS. 2A-2H illustrate embodiments of a surgical broach 200 as part of a suture anchor system comprising suture anchors of present embodiments. One or more embodiments may utilize suture anchors along with a surgical broach to prepare the bone for anchor insertion so as to achieve optimal suture or suture tape trajectory. The surgical broach 200 may comprise a shaft 210 having a proximal end 212, a distal end 214, one or more fins 215 projecting outward from the shaft 210. In some embodiments, the one or more fins comprise external retention features 205 on an exterior surface of the fins 215. In many embodiments, the one or more external retention feature comprises a bump, a ridge, a rib, a thread, a scale, an extension, a protrusion, or a projection, a barb, a hook, a spike, or the like, or any combination thereof. The fins 215 may be tapered, reducing in width from the shaft distally (e.g., the width at a proximal end of the fin is greater than a width at a distal end of the fin, wherein the width is measured from the shaft).

Figure 2A:
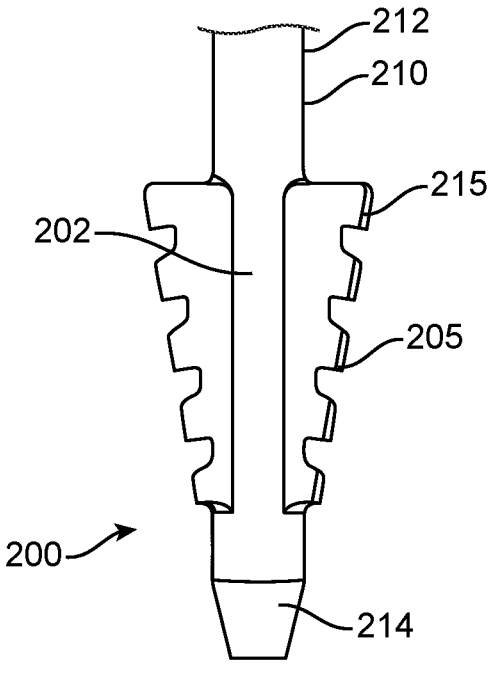
FIG. 2A shows a front view of a surgical broach, in accordance with some embodiments.
Figure 2B:
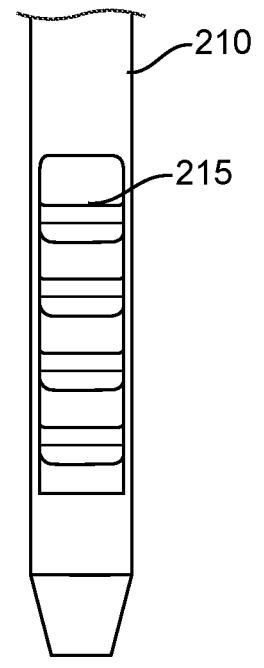
FIG. 2B shows a side view of a surgical broach, in accordance with some embodiments.

In some embodiments, as described herein, a surgical broach 200 is configured to modify a bone hole to have a shape matching the tapered configuration of the fins on the broach (see for e.g., FIG. 2A). Accordingly, a suture inserted with an anchor body that is subsequently inserted within the bone hole will permit the suture to follow the tapered (or sloped) path of the bone hole, and thereby reduce the angle at which the suture exits the bone hole at the bone hole opening (see for example FIG. 2H, 9). In some embodiments, the reduced angle may reduce the stress or tension experienced by the suture in some cases, thereby improving the integrity and tenure.

In some embodiments, the length of the broach within the bone hole is only to the location of a suture passage inserted with the anchor body within the bone hole. Accordingly, providing an anchor body as described herein, wherein the location of the suture passage is optimized (e.g., with reference to locating more proximally as described herein), would minimize the length of the broach within the bone hole, thereby limiting any reduction in pullout strength of the anchor body due to a reduced contact of the external retention features of the anchor body with the bone due to the tapered (or sloped) bone hole configuration.

Figure 2C:
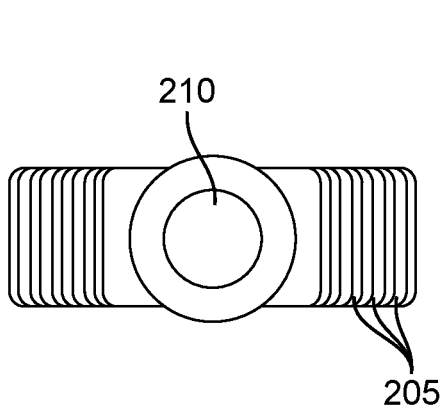
FIG. 2C shows a top view of a surgical broach, in accordance with some embodiments.
Figure 2D:
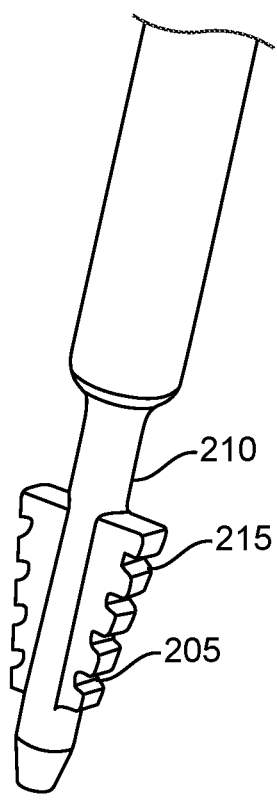
FIG. 2D shows a perspective view of a surgical broach, in accordance with some embodiments.
Figure 2E:
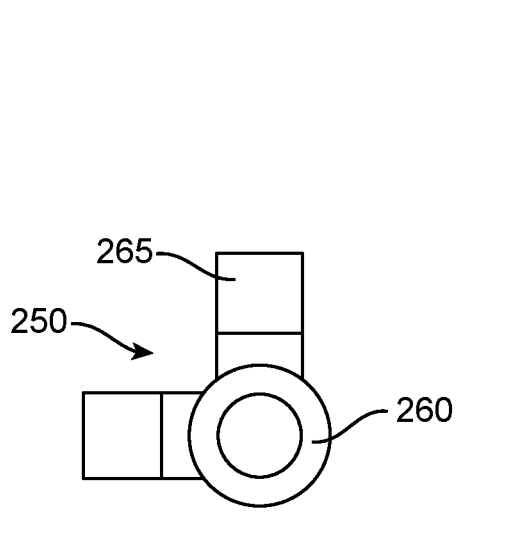
FIG. 2E shows a top view of another surgical broach, in accordance with some embodiments.
Figure 2F:
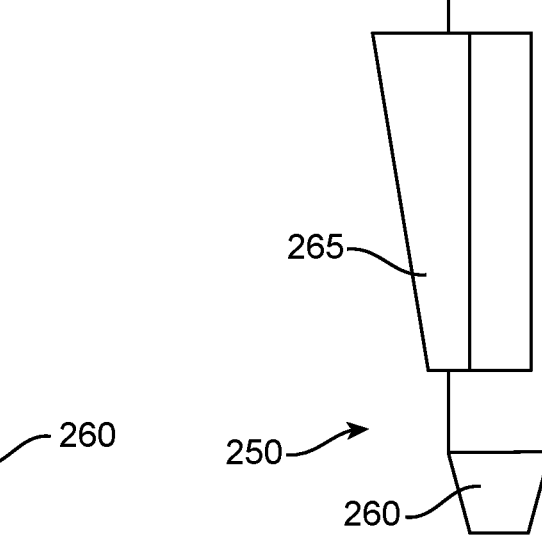
FIG. 2F shows a front view of another surgical broach, in accordance with some embodiments.
Figure 2G:
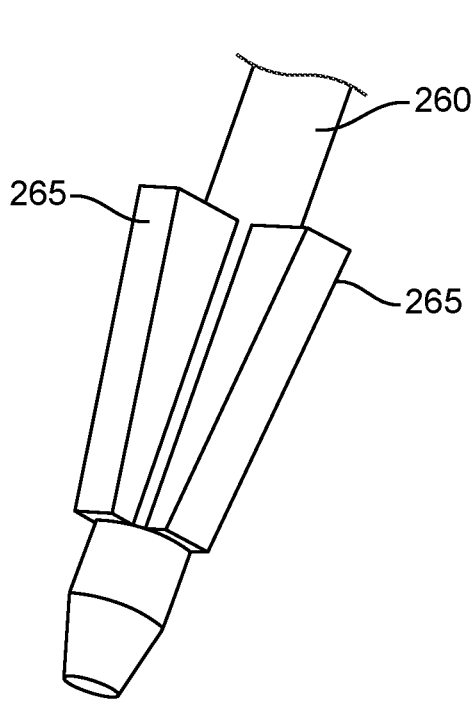
FIG. 2G shows a perspective view of another surgical broach, in accordance with some embodiments.

As depicted in FIGS. 2C-2D, a surgical broach comprising two fins 215 may project outwards from the shaft 210 in opposite directions. The angle between the fins 215 may be approximately 180 degrees. In other embodiments, the fins of a surgical broach described herein project outward from the shaft with an angle that is less than 180 degrees between each fin, (for example, the angle between each fin projecting outward from the shaft may be approximately 90 degrees). In other embodiments, the angle between the broach wings may be 30, 45, 60 degrees, or another measurement. There may be more than two such fins, for example, three fins, or four fins. The number of fins and the angle between them may be determined based upon the location of implantation for the anchor assembly.

In some embodiments, the wing width 220 (see FIG. 2I) of the surgical broach may be greater than or equal to the thickness of the suture passing through the anchor to enable the suture to slide, and to enable good suture trajectory (e.g., alignment in an anatomically natural direction). For example, in the case of a #0 surgical suture (USP size designation) with an average diameter of 0.375 mm, and a 3.5 mm suture anchor, the width of each wing may be approximately 0.375 mm from the shaft, and the total broach width from the center of the shaft to the end of a wing may be 3.875 mm; in the case of a #3 surgical suture (USP size designation) with an average diameter of 0.65 mm, and a 3.5 mm suture anchor, the width of each wing may be approximately 0.65 mm from the shaft, and the total broach width from the center of the shaft to the end of a wing may be 4.15 mm; in the case of a #5 surgical suture (USP size designation) with an average diameter of 0.75 mm, and a 3.5 mm suture anchor, and the total broach width from the center of the shaft to the end of a wing may be 4.25 mm. In embodiments where the wings of the broach are aligned in a 180 degree angle, the total broach width may be greater, for example, in the case of a #5 surgical suture (USP size designation) with an average diameter of 0.75 mm, and a 3.5 mm suture anchor, the total broach diameter 5.0 mm. As it is described in this paragraph, the wing width refers to the length of the wing across the wing from the point where it projects off of the broach shaft 210.

In some embodiments, the shaft 210 diameter of the broach 200 may be equal to that of the suture anchor intended to insert into the bone hole that the broach tool is preparing. For example, the circular outer diameter of the shaft 210 may be 3.5 mm in the case of a 3.5 mm suture anchor, 4 mm for a 4 mm suture anchor, etc.

Figure 2H:
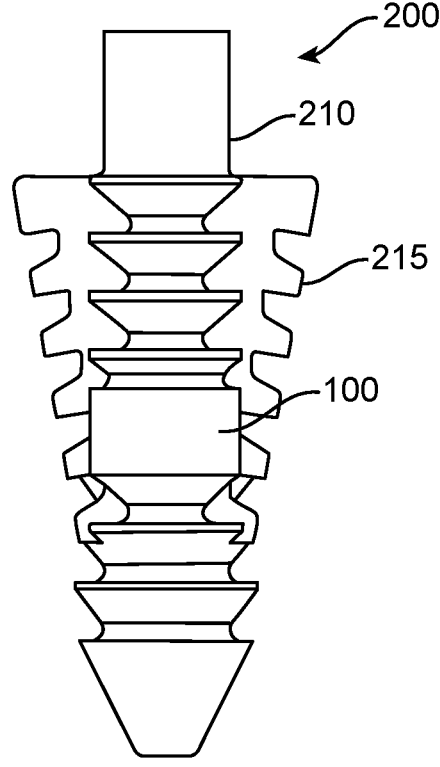
FIG. 2H shows a side view of a surgical broach relative to a suture anchor, in accordance with some embodiments.

In some embodiments, the wing depth 222 (see FIG. 2I) may be less than or equal to the distance from the centrally located suture passage in the suture anchor, and may only extend down the suture anchor to the position of the centrally located suture passage (for example, see FIG. 2H). In some embodiments, the wing depth may extend down to just below the centrally located suture passage. Because, in some embodiments, the broach wing depth may only extend down to the bottom of the centrally located suture passage; the bottom of the bone pilot hole will be unaltered by the surgical broach, and the external retention features on the suture anchor and below the centrally located suture passage will dig into additional cancellous bone tissue, and increase the pull out strength of the suture anchor. Additionally, because some embodiments of the surgical broach will only utilize two wings (e.g., aligned in a 180 angle, or at a 90 degree angle relative to one another), there will still be approximately half of the bone pilot hole which will be unaltered by the surgical broach, and the external retention features on the suture anchor on the unaltered sides of the bone pilot hole will dig into the cancellous and cortical bone tissue, and increase the pull out strength of the suture anchor. As it is described in this paragraph, the wing depth refers to the length of the wing from the flat upper surface of the wing positioned normal to the top of the shaft, to the bottom of the distal end of the wing at the bottom of the shaft.

In some embodiments, the wing height 226 (see FIG. 2I) may be greater than or equal to the width of the suture passing through the suture anchor, to enable the suture to slide, to enable good suture trajectory (e.g., alignment in an anatomically natural direction). For example, in the case of a #0 surgical suture (USP size designation) with an average diameter of 0.375 mm, the wing height may be 0.375 mm; in the case of a #5 surgical suture (USP size designation) with an average diameter of 0.75 mm, the wing height may be 0.75 mm; etc. As it is described in this paragraph, the wing height refers to a thickness of the wing when viewed from the top of the broach (e.g., FIGS. 2C, 2E), where the width is perpendicular to the direction where the broach wings contact the broach shaft.

In some embodiments, the size of the broach 200 may be configured to remove as little bone as possible, while still creating a pathway for the suture(s) to slide within the suture groove, have an anatomical trajectory (e.g., not bending around a 90 degree corner), and to align and pull on the soft tissue at more anatomically correct angles. For instance, if the broach wing width is too large, it may remove more bone outside of the suture anchor outer diameter, and the external retention features along that portion of the bone pilot hole will not function, decreasing the force needed to pull out the anchor and cause system failure. The improved surgical broach of one or more embodiments described herein may be configured to remove as little additional bone as possible, while preparing the bone pilot for proper suture alignment and trajectory, so as to reduce friction placed on the suture by the bone, permit for the soft tissue tethered to the suture to be pulled toward the anchor at a more anatomically correct angle, reducing suture failure, increasing the lifespan of the suture anchor system, and improving patient outcomes.

In some embodiments, the circular outer diameter 224 is equal to or smaller than a drill outer diameter.

In some embodiments, the configuration of the broach wings may correspond to the suture anchor being utilized in the repair, and may prepare the bone for the suture tape which will contact it. For example, considering the case of the improved Brostrom repair procedure described below, when utilizing a suture anchor with a suture passage orientated at a 90-degree angle; a broach 250 with wings 265 orientated at a 90 degree angle may be utilized. In another embodiment, when utilizing a suture anchor 100 with a suture passage orientated at 180 degrees, a broach 200 with wings 215 orientated at a 180 degree angle may be utilized.

The surgical broach may be used for preparing a hole drilled in bone for the insertion of an anchor body described herein. The surgical broach may be used to prepare the bone surface adjacent to the anchor and, for example, may be inserted into a hole in bone, and malleted in until the fins are at or just below the surface of the cortical bone in order to prepare the bone for anchor insertion. The compression of the cancellous bone tissue and removal of bone debris from the bone prior to anchor insertion may enhance attachment of the anchor to the bone. In some embodiments, the compression of the bone tissue along the upper part of the pilot hole may also broaden the pilot hole along the perimeter of the broach wings, and compact and smooth the surface of the bone along the perimeter of the wings. Because, in some embodiments, the wings are intended to align with the direction of the suture channel; the compression of the bone tissue along the upper part of the pilot hole may serve to increase the amount of space for the suture to run along the suture groove and away from the bone. In providing a pilot hole with increased diameter in directions parallel to the suture groove, sutures of greater width, size, or diameter can be accommodated, while placing less friction on the suture from the bone. In addition, the compression of the cortical bone tissue by the broach along the edges and surface of the bone tissue may smooth the edges of the bone which contact the suture as it runs out of the bone and into the soft tissue it is attached to. Smoothing the edges of the bone which contact the suture may also reduce fiction placed on the suture by the bone and reduce wear on the suture, extending the useful life of the suture anchor system.

Potential benefits of utilizing a suture anchor system with a broach tool include improved suture anchor system pull out strength, are anatomical pulling of the ligaments, improved bone leading around all sides of the suture or suture tape, an increased ability to tension the suture, improved suture trajectory angles, and optimal healing for artificial grafts. In some embodiments, utilizing a surgical broach tool can help to compact the cancellous bone tissue and cortical bone tissue along the length of the suture groove in order to provide additional space for the sutures, improving the ability of a suture to slide within the suture groove, and a surgeon's ability to tension the suture following anchor insertion. The surgical broach may result in smooth or rounded edges or corners along the cortical bone surface where the suture contacts the bone, allowing the suture to pull the suture anchor at an angle other than 90 degrees, increasing the pull out strength of the suture anchor system, including in combination with other features of the suture anchor system. For example, bone compaction with the surgical broach and the smooth curves along the cortical bone surfaces as a result thereof in combination with the uppermost rounded recess of the suture anchor may further increase the displacement from 90 degrees at which the suture pulls on the suture anchor, further increasing pull out strength of the suture anchor relative to pull out strength if the force was applied at a 90 degree angle. The compacting of the bone tissue surrounding the suture groove and suture may also allow the bone to heal around all sides of the suture or suture tape. For example, when working in combination with the increased ability to tension a suture resulting from the use of the surgical broach, the competed corner profile resulting from use of the surgical broach which permits the bone to heal around all sides of the suture may optimize healing for an artificial graft.

In some embodiments, the surgical broach may have a variable wing depth which extends down to the bottom of the suture anchor. Such deep wing embodiments may be useful in embodiments of the suture anchor which have a distally located suture passage as opposed to a centrally located suture passage. In embodiments of the extended wing depth broach, the wings may be tapered at an increased angle as they move down the broach shaft to reduce the amount of bone compressed or removed by the broach, as to maintain adequate contact between the bone tissue and the external retention features of the suture anchor.

In some embodiments, broach may have only one wing, and such single wing surgical broaches may be useful in preparing bone pilot holes at the end of a system where they are the beginning or the end of a suture tape assembly, and only receive a single suture tail.

Referring to FIGS. 3A-3C, in some embodiments, an anchor system described herein further comprises a suture anchor delivery device 300/350 for surgically inserting the suture anchor 100. The delivery device may comprise a shaft 310, a handle 317, a rotating base 319 which rotates an internal driver within the shaft 310, and one or more alignment markings 321/371 disposed thereon. The alignment markings 321/371 may be used to align the delivery device 300/350, and therefore the anchor body 115, to a desired position within a bone such that a suture 310 aligns as desired with respect to a portion of soft tissue for repair. The anchor body 115 and the delivery device 300/350 are shown in a delivery configuration with the alignment markings 321/371 aligned to the suture groove 145. The rotating base 319 may rotate an internal driver which may screw in an insert placed within the suture anchor, as to compress the suture between the insert and the distal end of the suture passage.

The delivery devices may further comprise one or more suture cleats 305/355 which may be used to tension a suture prior to insertion of the suture anchor. The suture cleats may generally be in the shape of hooks, or a projecting structure which has a first section that extends outward from the handle of the delivery device 300/350 approximately at a 90 degree angle, and which then turns and extends backwards towards the rear of the handle of the delivery device, for example, at a 90 degree angle, 60 degree angle, or other angle between 90 and 0 degrees, as to create a surface upon which the suture 310 may be wrapped around and tensioned. There may be one or more slits or slots in the surface of the suture cleats to further secure the suture 310 in place.

There may also be provided a threading tool 400 to assist a surgeon in threading the suture passage 110 with a suture 310.

Figure 4A:
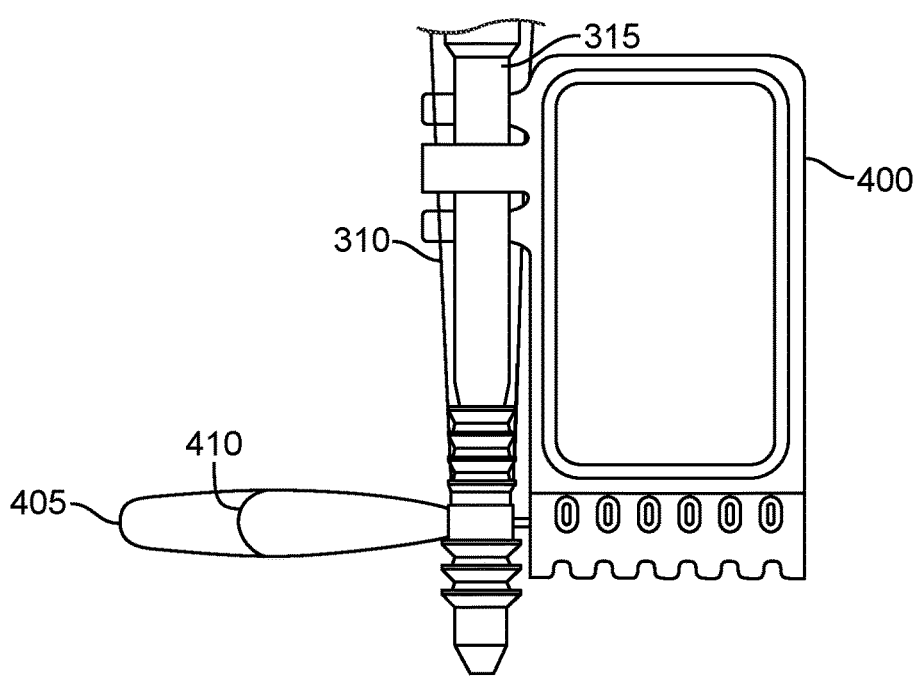
FIG. 4A shows a close up front view of the anchor placed within another delivery device and attached to a suture threading tool, according to some embodiments.

FIG. 4A shows a close-up view of the delivery device 300, suture anchor 100, and the threading tool 400 pictured in FIGS. 3C-3C. The threading tool 400 may comprise one or more clips which hold it onto the shaft 315 of an insertion tool 300. There may be three clips 415, two on a rear side of the threading tool 400, and one on a front side of the threading tool 400, which hold the shaft of the 315 of an insertion tool 300 in between them. The threading tool may further comprise two loops which extent outwards from the bottom of the threading tool. There may be a first loop 405 which extents outwards from the bottom of the threading tool, and a second loop 410 which is within the first loop 405, and extends outwards from the bottom of the threading tool at a distance shorter than the first loop. A one or more sutures 310 may then be threaded through the first loop 405, the second loop 410, or both, and the threading tool 400 may then be pulled out from the suture passage with the suture 310 still inserted, as to thread the suture 310 through the suture passage.

In one or more embodiments, threading the anchor with a suture comprises inserting a suture through the suture passage in the anchor body. In some embodiment, threading the anchor with a suture comprises utilizing the threading tool to thread the suture anchor by inserting the loops of the threading tool through the suture passage, clipping the threading tool onto the anchor and/or the delivery device, passing the suture through the loops of the threading tool, and pulling the tab of the threading tool to pull the loops and the suture through the suture passage of the anchor, threading the anchor with the suture.

Figure 4B:
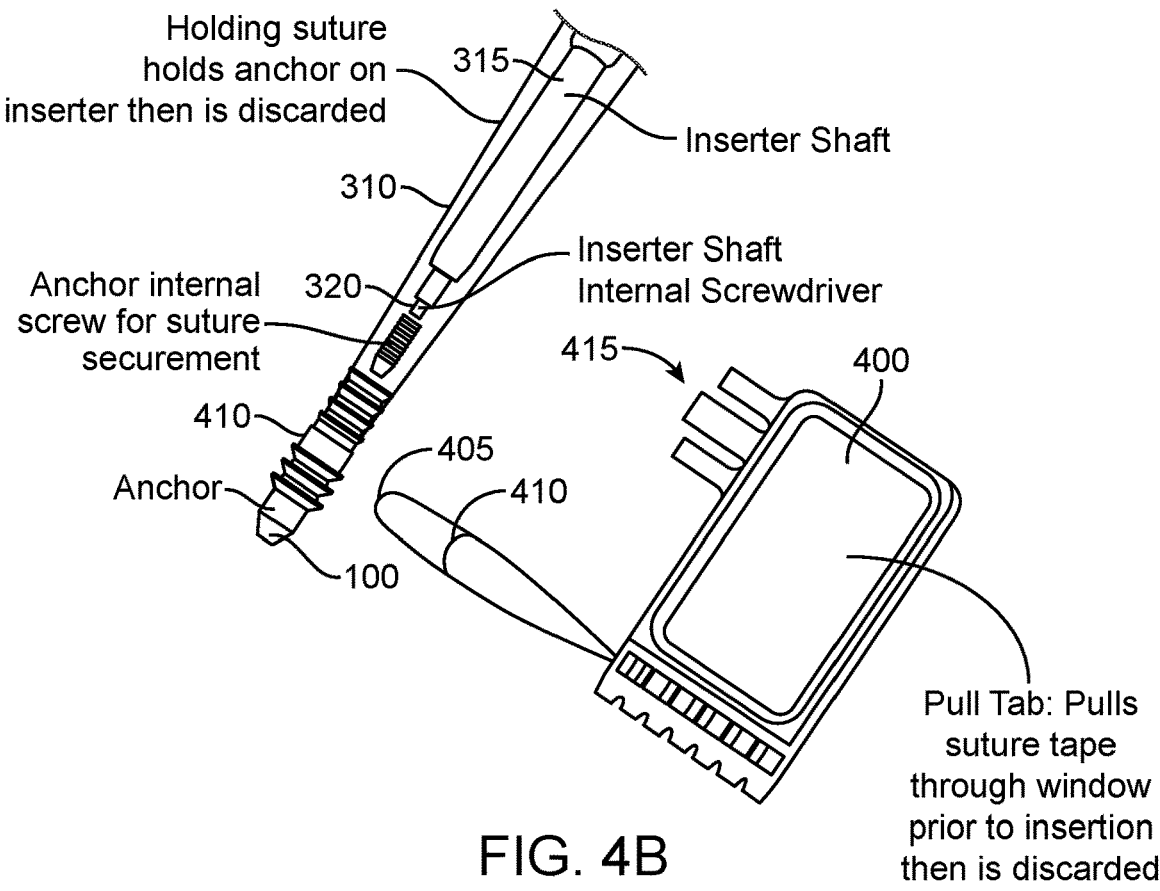
FIG. 4B shows an exploded view of the anchor placed within another delivery device and attached to a suture threading tool, according to some embodiments.

FIG. 4B shows a close up exploded view of the delivery device 300, suture anchor 100, and the threading tool 400 pictured in FIGS. 3B-3C. Shown is the insertion device 300, the insertion device shaft 315, the suture 310 threaded through the suture anchor 100, and the suture anchor 100 attached to the insertion device 300. Also shown is the suture anchor insert 140 and the delivery device internal driver 320 which is configured to rotate and screw in the suture anchor insert 140 into the anchor body 115 when the rotating base 319 on the handle 317 of the delivery device 300 is rotated. When the suture anchor insert 140 contacts the distal end of the suture passage 110, it will compress the suture 310 between the distal end of the suture passage and the insert, holding it in place, and possibly the surgeon to tension the suture 310 without forming a knot.

Figure 5:
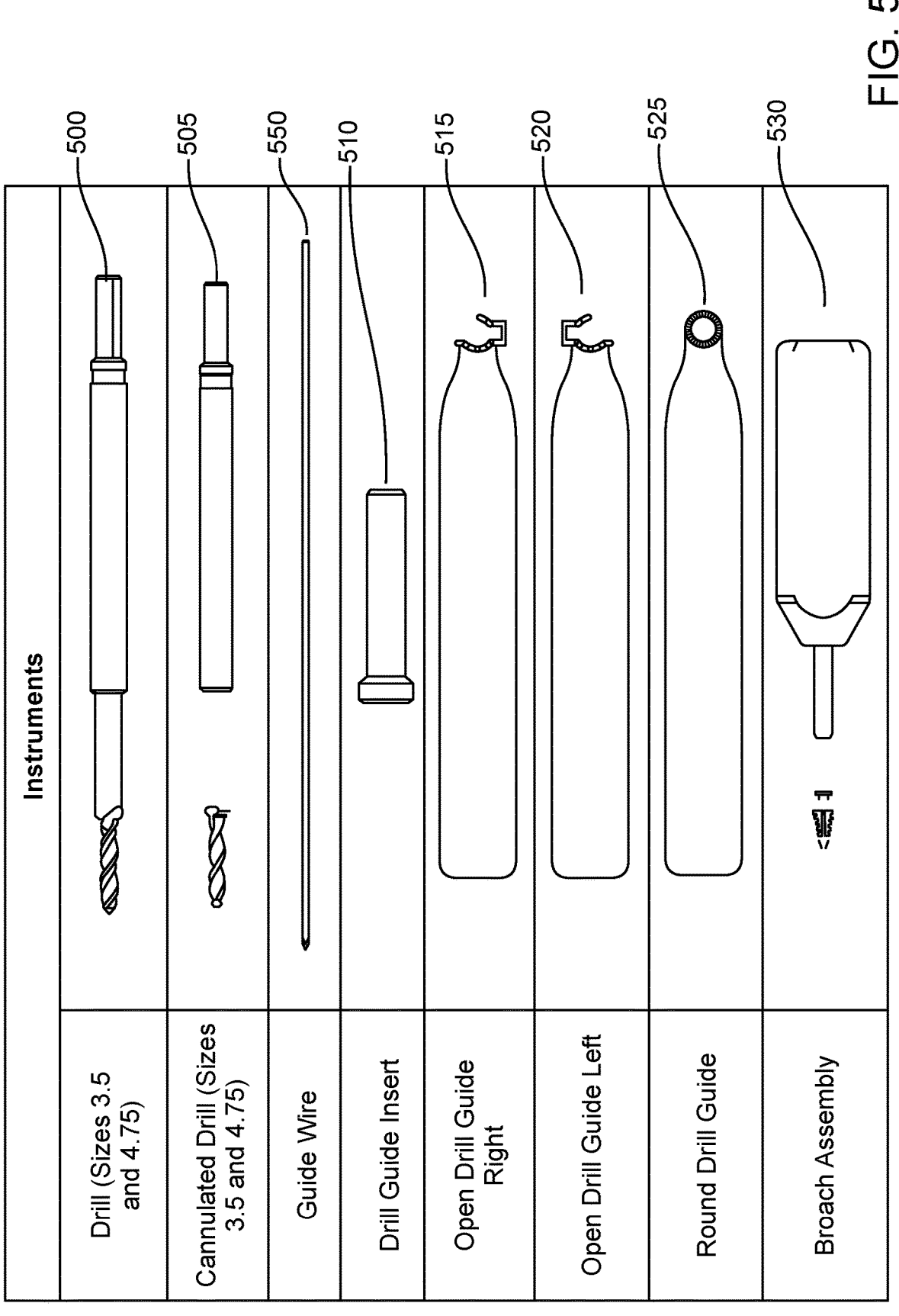
FIG. 5 shows front a view of various surgical tools for use with suture anchors of some embodiments.

In some embodiments, there may be provided a suture anchor kit. Various possible components of the suture anchor kit are shown in FIG. 5. For example, there may be included a suture anchor drill 500, possibly sized at 3.5 and 4.75 mm; a cannulated drill 505, possibly sized at 3.5 and 4.75 mm; a guide wire 510; a right sided open drill guide 515; a left sided open drill guide 520; an enclosed drill guide 525; and a broach assembly apparatus 530. Not all of these components may be included in the suture anchor kit, and only two, or any combination thereof, may be included in the kit, as well as other possible components.

The suture 310 may be positioned within the suture passage 110 with a first end extending proximally out of the first opening 136 and along the first suture groove 145 and a second end extending proximally out of the second opening 138 in the second lateral side 126 of the anchor body 115 and along the second suture groove 74 running parallel to the longitudinal axis 116 of the anchor body 115 and extending from the second opening 138 to the proximal end 112. The suture 310 may be recessed relative to the one or more external retention features 118, possible within the suture groove 145 defined by the plurality of rounded recesses 105, as to ensure that the suture 310 disposed therealong does not protrude outward past the external retention feature(s) 118 to contact the bone when the anchor is inserted therein. The recessed suture 310 can slide freely within the suture passage 110 and along the first and second suture grooves 145 which allows for adjustment of suture tension after the anchor 100 has been positioned in the bone but before the suture 310 has been locked within the suture passage 110 as further described below.

In some embodiments, the suture 310 comprises a #2 UHMWPE braided suture. In some embodiments, the suture 310 comprises a suture tape. In some embodiments, the suture 310 comprises a flat braid configuration. In some embodiments, the suture 310 comprises a round to flat braid configuration. In one or more embodiments, the suture 310 comprises a 2.3 mm round to flat tape suture. Such a round to flat tape suture may enable a bone tunnel from the fibula in one or more embodiments disclosed herein.

In some embodiments, the suture 310 is made from other non-absorbable suture materials, such as polyester. In some embodiments, the suture 310 may be made from an absorbable suture material, such as polyglactin (PGLA). In some embodiments, the suture 310 has a tapered tail for ease of passing through the body.

FIGS. 3A-3C shows a front view of a delivery device 300/350. The delivery device 300/350 comprises an outer shaft 315, an inner shaft, a driver 320, and a handle 317. The outer shaft 315 optionally comprises rotational markings 321/371 as described herein. The inner shaft is configured to engage a proximal end of the anchor body 115 (e.g., with a proximal portion of the channel 144) during anchor delivery. In some embodiments, the inner shaft may be inserted into a proximal portion of the channel and may engage with an inner surface of the channel. In some embodiments, the inner shaft is longitudinally translatable relative to the outer shaft 315 so as to facilitate delivery and release of the anchor 100 therefrom. In some embodiments, the inner shaft and the driver 320 are translatably disposed within the outer shaft 315. The driver 320 is configured to couple to a device coupler of the insert 140 and facilitate longitudinal translation of the insert 140 within the channel of the anchor 100. The delivery device 300/350 optionally comprises a rotating base 319 disposed on the handle 317. The base 319 may be operably coupled to the driver 320 and configured to transmit rotational motion to the driver 320 (and from there to the insert 140). Rotation of the base 319 may rotate the insert 140 along its threading and longitudinally translate the insert 140 within the anchor 100 as described herein. In some embodiments, the base 319 can be replaced with a strike plate to enable impaction of the implant instead of rotation thereof depending on the method of translation desired.

In some embodiments, the delivery device 300/350 positions the anchor 100 within a pre-formed hole in a bone. The delivery device then rotates, axially impacts, or otherwise longitudinally translates the insert 140 relative to the anchor 100 to lock a suture within the anchor body 115. In some embodiments, the pre-formed hole is generated using a drill. In some embodiments, the pre-formed hole is generated using an awl.

In some embodiments, the inner shaft, outer shaft 315, and/or driver 320 comprise stainless steel. In some embodiments, the inner shaft, outer shaft 315, and/or driver 320 comprise hardened steel alloy.

In some embodiments, the inner shaft, outer shaft 315, and/or driver 320 are cannulated.

In some embodiments, the inner shaft, outer shaft 315, and/or driver 320 are knurled at the opposite end from anchor 100 to facilitate handle attachment.

In some embodiments, the handle 317 comprises plastic. In some embodiments, the handle 317 is overmolded. In some embodiments, the handle 317 comprises Makrolon. In some embodiments, the handle 317 comprises ABS. In some embodiments, the handle 317 comprises glass-filled ABS. In some embodiments, the handle 317 is coupled to the outer shaft 315 with a medical-grade adhesive. In some embodiments, the handle 317 is coupled to the outer shaft 315 with a press-fit.

In some embodiments, the delivery device 300/350 has depth markings. The depth markings may help surgeons to determine how far the delivery device 300/350 has been placed within a patient. In some embodiments, delivery device 300/350 may have laser marking(s) showing suture orientation (e.g., rotational markings 321/371 shown in FIG. 1) and proper insertion depth.

In some embodiments, the anchor 100 may be placed within a patient using a device or devices other than delivery device 300/350. Examples of additional insertion devices that may be used to implant the anchor 100 into a patient include manual insertion with standard surgical instruments. In some examples, an insertion device may include a lighting and/or camera component so as to help guide a surgeon when placing the anchor within a patient.

In some emblements, the suture 310 is wrapped around cleats 305 on handle 317 of the delivery device 300/350. In some instances, the surgeon may utilize the cleats to hold tension on the suture 310 and/or anchor 100 during the implantation procedure. Alternatively, or in combination, the suture 310 is wrapped around the cleats 305 in order to hold the anchor 100 in position against the distal end of the delivery device 300/350 prior to implantation (e.g., during shipping or preparation of the surgical site).

In some embodiments, the delivery device 300/350 comprises an outer shaft 315, an inner shaft, and a driver 320. In some embodiments, the inner shaft and the driver 320 are translatably disposed within the outer shaft 315. The driver 320 is configured to couple to a correspondingly-shaped device coupler of the insert 140 and facilitate longitudinal translation of the insert 140 within the channel of the anchor 100. In some embodiments, the driver 320 is a male driver 320 having a shape corresponding to a cavity in the insert 140. In some embodiments, the driver 320 is a female driver 320 having a shape corresponding to a proximal protrusion of the insert 140. The driver 320 may be operably coupled to the insert 140 and configured to transmit rotational motion to the insert 140. In some embodiments, rotation of the driver 320 relative to the inner shaft and/or outer shaft 315 may rotate the insert 140 along its threading and longitudinally translate the insert 140 within the anchor 100 as described herein. In some embodiments, the driver 320 may be operably coupled to the insert 140 and configured to impact the insert 140 in addition to or instead of rotating the insert 140.

In some embodiments, the delivery device 300/350 may comprise an inner shaft and a driver 320 as described herein. The inner shaft and the insert 140 may be rotationally coupled to one another. Rotation of the driver 320 relative to the inner shaft rotates the insert 140 within the channel 144 relative to the anchor body 115 in order to translate the insert 140 therewithin along the threads of the channel and the insert 140 as described herein.

FIG. 6 shows an exemplary method of use for any of the anchors 100, kits, assemblies, or systems described herein.

At Step 600, the repair site may be prepared. It will be understood by one of ordinary skill in the art that repair site may be prepared based on the anatomy, expertise of the surgeon, and/or preference of the surgeon. The anchor device 100 may, for example, accommodate an open, mini-open, and/or arthroscopic surgical approach as desired.

At Step 600, the tissue for reattachment may be prepared according to a preferred surgical technique of the surgeon. In at least some instances, the anchor is pre-loaded with a suture. In other instances, the suture is not pre-loaded with a suture.

At Step 605, the bone may be prepared to receive the anchor. For example, a pre-formed or pilot hole may be formed. In some embodiments, the pilot hole is formed using an anchor drill. In some embodiments, the pilot hole is formed using an awl. In some embodiments, a tip of an awl may be placed at a desired anchor site. The shaft may be aligned in line with the intended anchor axis orientation. A surgeon may then mallet the awl handle until a desired depth has been reached.

One or more drill guides may be provided to accommodate varying anatomy and preferences. The drill guide(s) may be placed at a desired anchor site, the shaft of which may be aligned with the intended longitudinal axis of the anchor. A standard surgical power drill, or a specialized elongated anchor drill coupled to a surgical power drill, may be inserted into the drill guide until the drill is near the bone surface. One or more markings may be provided on the drill or drill guide for visualization. The drill may be used to create a pilot hole. A collar on the drill may be configured to bottom out on the drill guide in order to ensure that the pilot hole does not exceed a pre-determined proper hole depth. The guide tube and/or drill may then be removed.

At Step 610, the suture anchor may be inserted into the bone. For example, a delivery device as described herein may be positioned adjacent to the bone with the distal end of the anchor body adjacent to the bone. In some embodiments, the anchor is adjacent to a pre-drilled hole in the bone. The delivery device may rotate, impact, or otherwise drive the anchor into the bone. For example, the inner shaft and/or outer shaft and/or a separate mallet of delivery device may be used to drive the anchor device into the bone. The anchor body may be inserted until an optional circumferential laser mark on the delivery device, or other identifying mark or feature, is fully beneath the bone surface or otherwise desirably positioned relative to the bone.

In some embodiments, the bone may not require a pre-formed hole and the anchor may be self-punching (e.g., having a pointed tip). The anchor may be driven into the bone without pre-formation (e.g., drilling) of a hole.

At Step 615, the suture 310 may be passed through or around the tissue intended to be secured to the bone as described herein. In some embodiments, the suture is passed through or around the tissue prior to the insertion of the anchor in the bone. In some embodiments, the suture is threaded through the anchor after insertion. In some embodiments, the suture is threaded through the anchor more than once, such as before and after anchor insertion.

At Step 615, the tissue may be repaired by passing the suture through the issue, and the suture may be tensioned and locked in the anchor. For example, a tail of the suture may be tensioned (e.g., pulled on) to a desired tension. In some embodiments, once the anchor is fully inserted, the suture tails may be pulled to the desired tension. Tails may be wrapped around the cleats on the inserter handle to maintain tension. Additionally, the knob may be rotated clockwise to drive the internal mechanism and secure the suture. The handle may be held steady during this process.

The delivery device may be configured to longitudinally translate an insert so as to engage a suture at the desired tension and may not be reversible (e.g., the anchor may comprise a one-way locking mechanism). In some embodiments, the anchor and/or insert may comprise an additional locking mechanism configured to lock the insert in the channel of the anchor after compressing the suture.

After locking the suture can be tied to another anchor and/or threaded through the suture passage as desired. Any extra length of suture exposed at the anchor interface may be cut and discarded.

At Steps 620 and 625, following installation and tensioning of a first suture anchor, the process may then be repeated in order to complete installation of additional suture anchors, as may be required by the particular surgery being completed.

At Step 625, the surgical broach 200 may optionally be inserted into the previously prepared anchor hole. Optionally, the open drill guide 515/520 may be used to position the surgical broach 200. The surgical broach 200 may be aligned with the drill guide 515/520 and may be advanced until it is at the bone surface. It may then be struck with a mallet to drive it into the bone until it bottoms out on the drill guide 515/520. Alternatively, the broach may be inserted without a guide by aligning the direction of the fins 215 with the targeted suture direction, and inserting the broach with a mallet until the top is just below the cortical layer of bone tissue. The broach wings should align with the intended trajectory of the suture and the suture groove of the suture anchor. In some embodiments, only the second and third anchor holes may be broached, and the initial anchor hole, or the central anchor hole which acts as a primary support for the suture network, may not be broached.

At Step 630, the suture 310 or suture tape may be loaded into the suture anchor 100 by using the suture threading tool 400. This may be accomplished by inserting the loops of the threading tool through the suture passage, threading the suture through the loops of the threading tool, and then pulling the loops backwards through the suture passage.

At Step 635, the second suture anchor may be inserted using a method similar to insertion of the first suture anchor.

At Step 640 the tissue may be repaired and the suture tensioned. The surgeon may pull upwards on the suture tails, evenly with increasing tension while keeping constant downward pressure on the insertion until the desired tension is reached. The surgeon may perform range of motion tests on the patient and tighten or loosen the suture tape until the desired tension is reached with the range of motion confirmation. Optionally, when tensioning the sutures or suture tape, the tails of the sutures may be placed around one of the suture cleats 305 of the insertion device 300 while pulling downwards to both tension the suture and apply downwards pressure to the inserter.

At Step 645, the process described in Steps 620-640 may be repeated for a third, or subsequent, suture anchor.

At Step 650, following installation of all suture anchors, and tensioning and locking of all sutures, the sutures may then be trimmed as necessary. The suture is then tensioned between the two suture anchors, and any remaining suture is cut flush with the anchor to complete the repair. The suture tails may be tied down so that they lie flush on the retinaculum. A 3.5 mm suture anchor approximately 8.5 mm in length, along with 1.3 mm suture tape may be utilized.

At Step 655, the repair site may then be closed, sealed, and sterilized as may be necessary to complete a successful surgical repair.

Although the steps above show a method of repairing a tissue with a suture anchor 100 in accordance with embodiments, a person of ordinary skill in the art will recognize many variations based on the teaching described herein. The steps may be completed in a different order. Steps may be added or deleted. Some of the steps may comprise sub-steps. Many of the steps may be repeated as often as necessary to repair a tissue.

It is noted by the Applicant that suture anchors of one or more embodiments improve soft tissue repair around the ankle because the high stress placed on the sutures due to the biomechanics fibular ligaments which are often the subject of surgical repair. For instance, the suture anchors of one or more embodiments allow sutures to run at more natural angles over the bone (e.g., other than 90 degree angles), or through bone, as may be desirable when repairing the ligaments of the ankle, such as the fibular ligaments.

Accordingly, one or more embodiments of suture anchors of and surgical methods of use for facilitating repair of soft tissue repair of the ankle are disclosed herein. Suture anchors of one or more embodiments may comprise a suture passage with first and second openings orientated in a first and second lateral surface of an anchor body that are orientated approximately 90 degrees relative to one another, may comprise a suture channel extending along the longitudinal axis of the anchor body from a proximal opening in the proximal end of the anchor body to a distal opening in the suture passage, and may allow for suture to be threaded through the suture anchor at the top of the anchor. Such embodiments may allow the suture to run outward from the anchor at an orientation of 90 degrees relative to its initial angle of entry, and may be uniquely optimized for facilitating repair of soft tissues in the ankle.

For instance, disclosed are surgical methods which utilize a single suture as a continuous thread for repair or support of a ligament in the angle, passing through two or more suture anchors. The suture anchors may permit such use of a single suture as a continuous thread by permitting the single suture to be tensioned at each suture anchor, and pass through each suture anchor at approximately 90 degree angles, permitting the suture anchor to enter in a first direction, and exit in a second direction. Such surgical methods using suture anchor systems of present embodiments may be useful for facilitating Brostrom repair procedures, improved Brostrom repair procedures described herein, or other surgical procedures repairing ligaments in the ankle.

Figure 8:
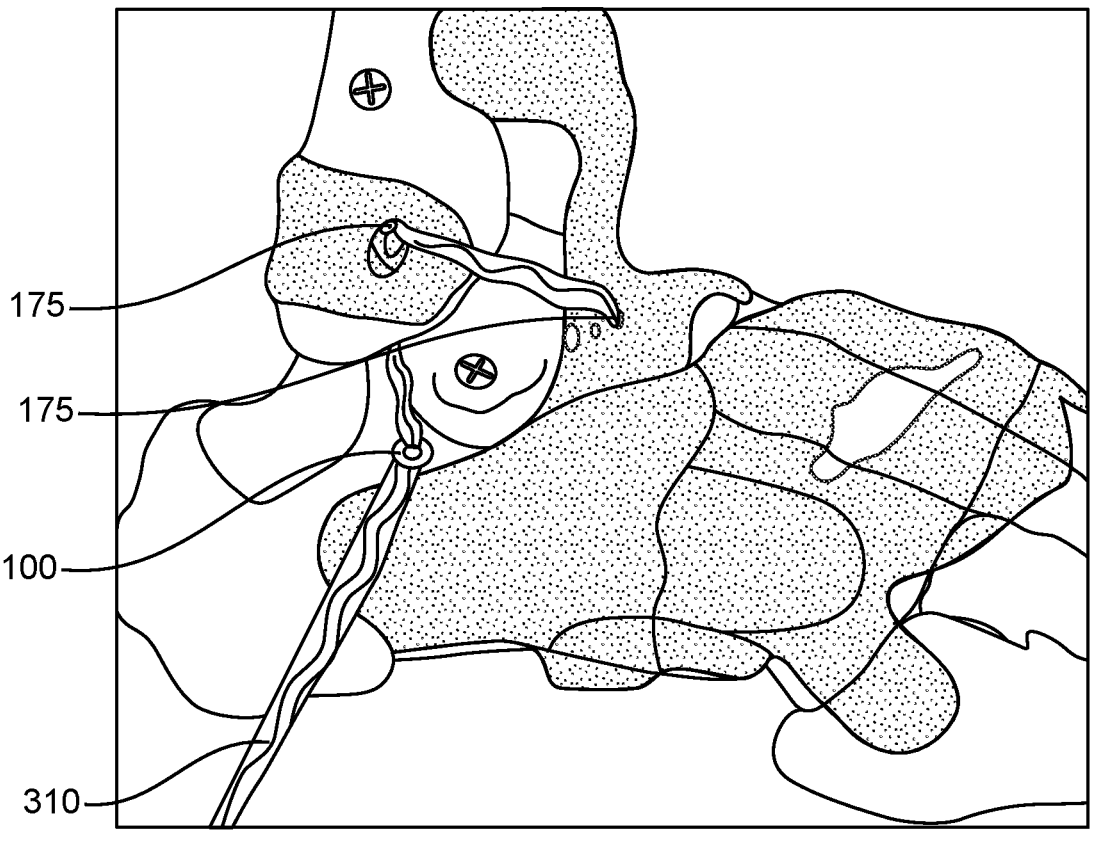
FIG. 8 shows a front view of completed surgery in which multiple suture anchors of some embodiments have been successfully implanted.

FIG. 8 demonstrates an exemplary embodiment of an improved Brostrom repair surgical procedure using the suture anchor system of one or more embodiments. The improved Brostrom repair surgical procedure may utilize a combination of 3 suture anchors, which attach to the talus, distal fibula, and calcaneus bones with a suture running between them in a triangular or seatbelt like manner. The use of a three-point suture anchor system with suture running extending outwards from the distal fibula and in different directions relative to one another may improve the support provided by the suture anchor system, joint flexibility, patient mobility, and overall patient outcomes. In one or more embodiments, one or more suture tails may run through the fibular bone tunnel to avoid ligament impingement. In addition, using suture anchors of one or more embodiments may also permit small diameter anchors to be used in the procedures because of the increased pull out strength, for example, 3.5 mm suture anchors as opposed to 4.75 mm suture anchors.

Suture anchors of one or more embodiments which allow sutures to exit the suture anchor in a direction that is 90 degrees (or approximately 90 degree) relative to the direction in which it entered the suture anchor, or through a bone tunnel (e.g., the fibular bone tunnel), as may be desirable when repairing the ligaments of the ankle, such as the fibular ligaments. For example, the suture may enter the suture anchor at the top of the suture anchor on the surface of the fibula, and may exit the suture anchor from the center of the suture anchor through the suture passage and through the fibula bone tunnel (for example, as show in FIG. 8). Similar embodiments may be utilized in other suitable anatomical areas as well, where suture enters the suture anchor from the proximal end of the suture anchor, and exits the suture anchor from the distal end of the suture anchor through the suture passage, or vice versa. In some embodiments, the angle between the initial trajectory of the suture and the exit trajectory of the suture may be greater or less than 90 degrees, for example, between 60 and 120 degrees.

Figures 7A, 7B:
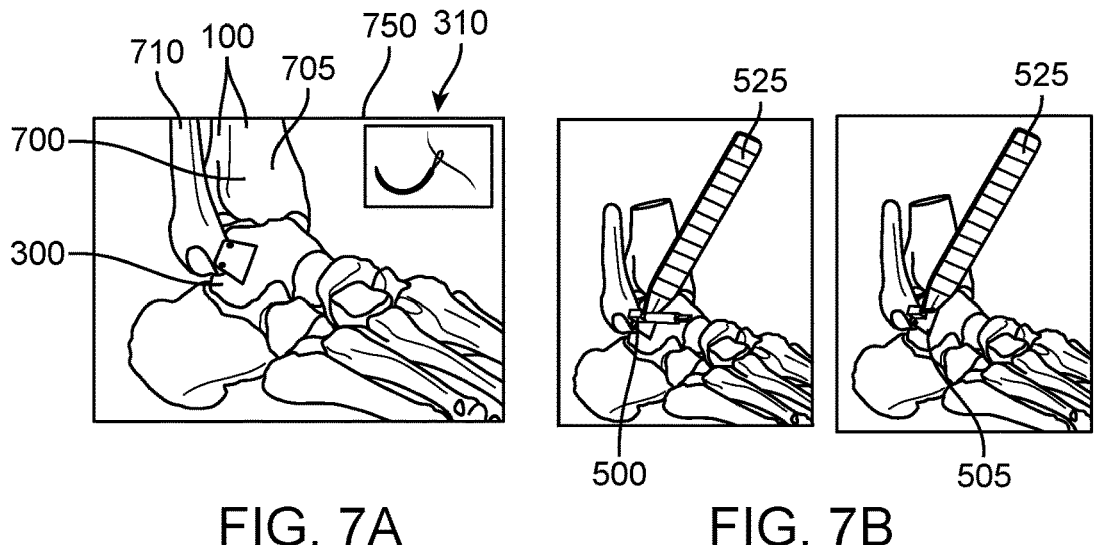
FIG. 7A shows a front view of a surgical site where one or more suture anchors of some embodiments will be implanted.
FIG. 7B-7R shows steps in a process by which one or more suture anchors of some embodiments will be implanted.
Figure 7C:
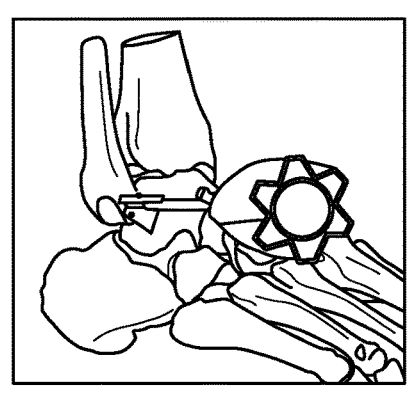
Figure 7D:
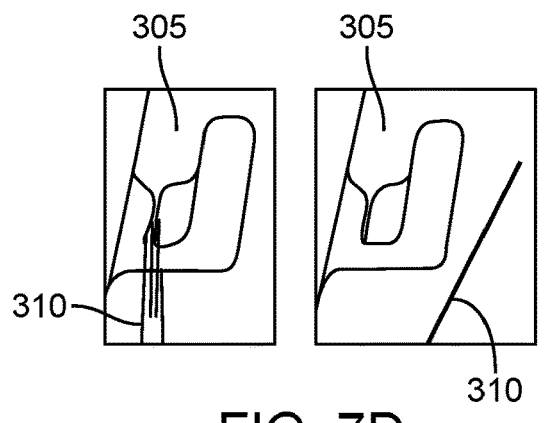
Figure 7E:
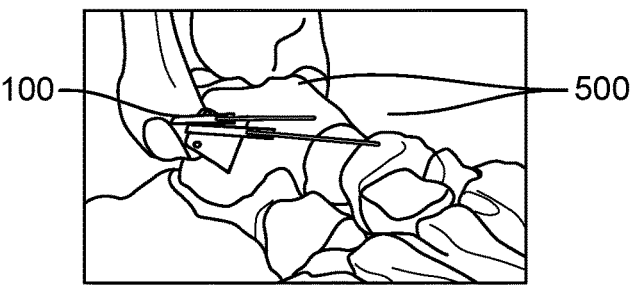
Figure 7F:
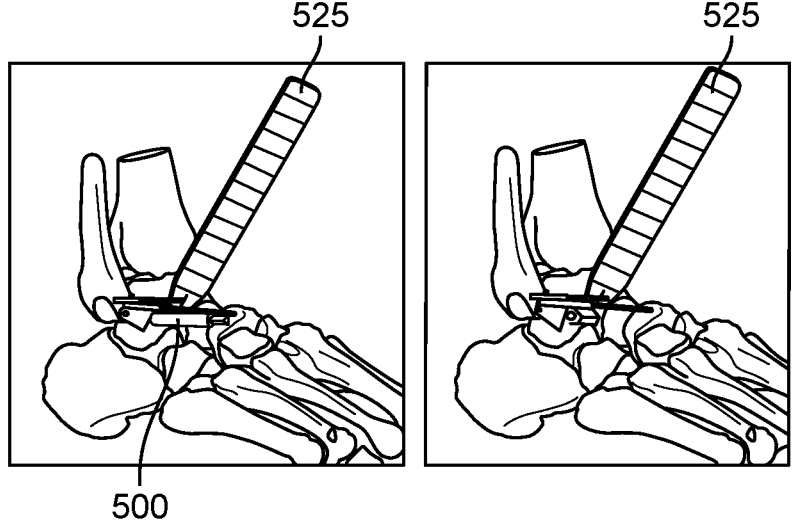
Figure 7G:
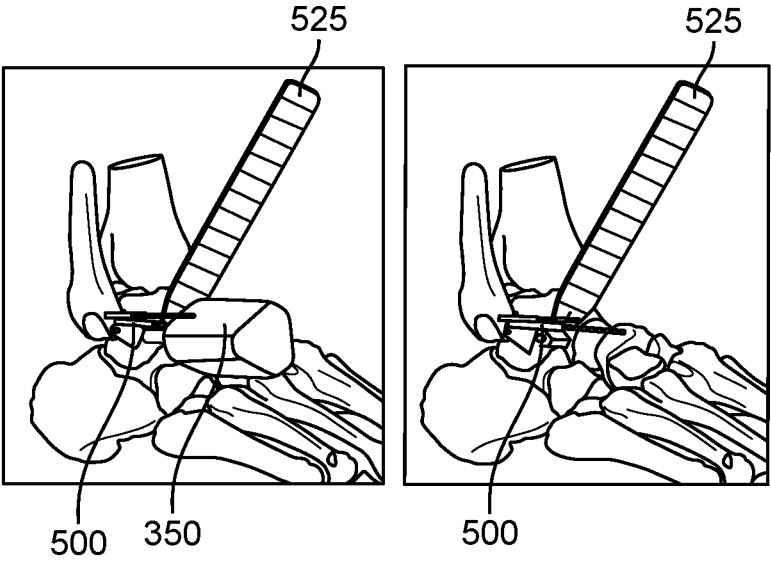
Figure 7H:
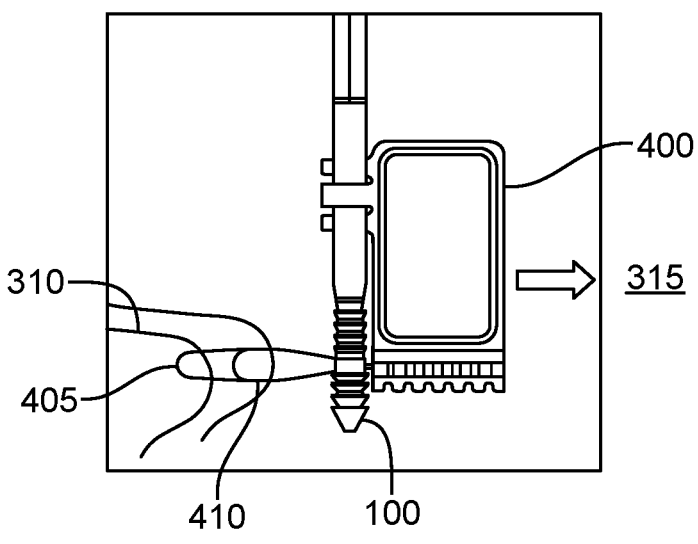
Figure 7I:
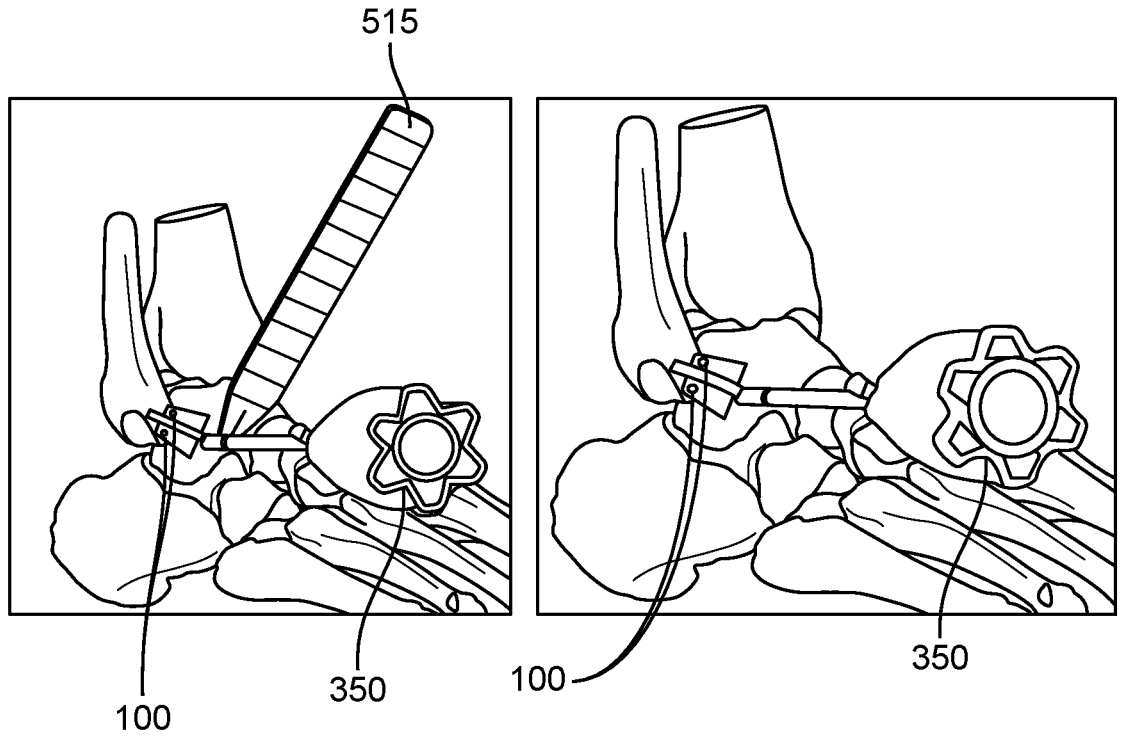
Figure 7J:
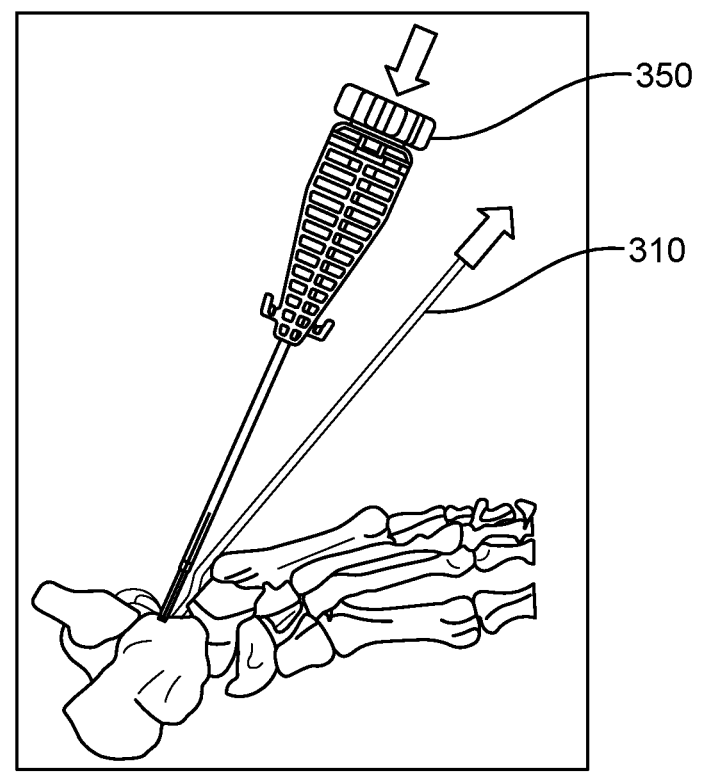
Figure 7K:
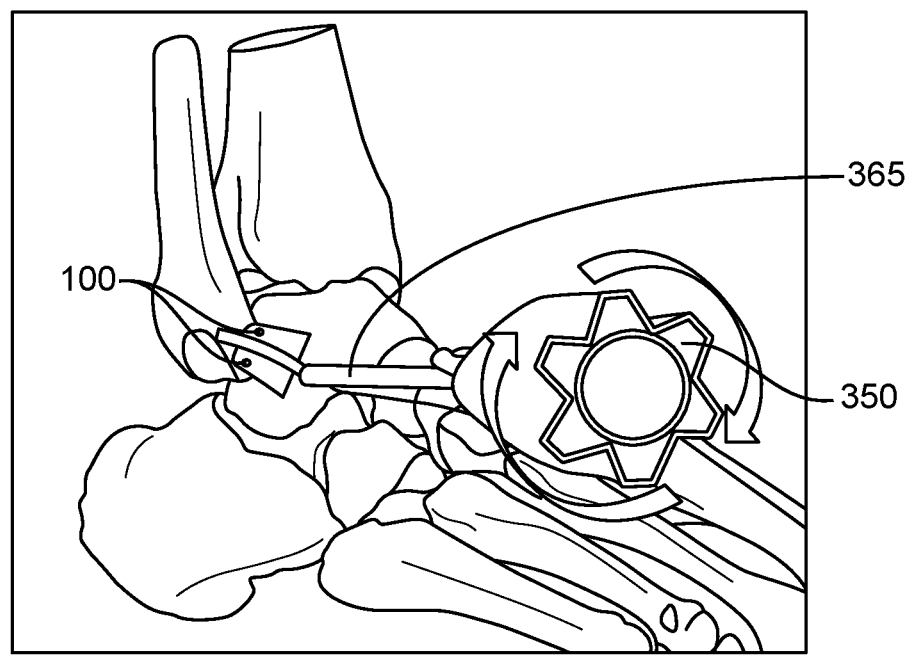
Figure 7L:
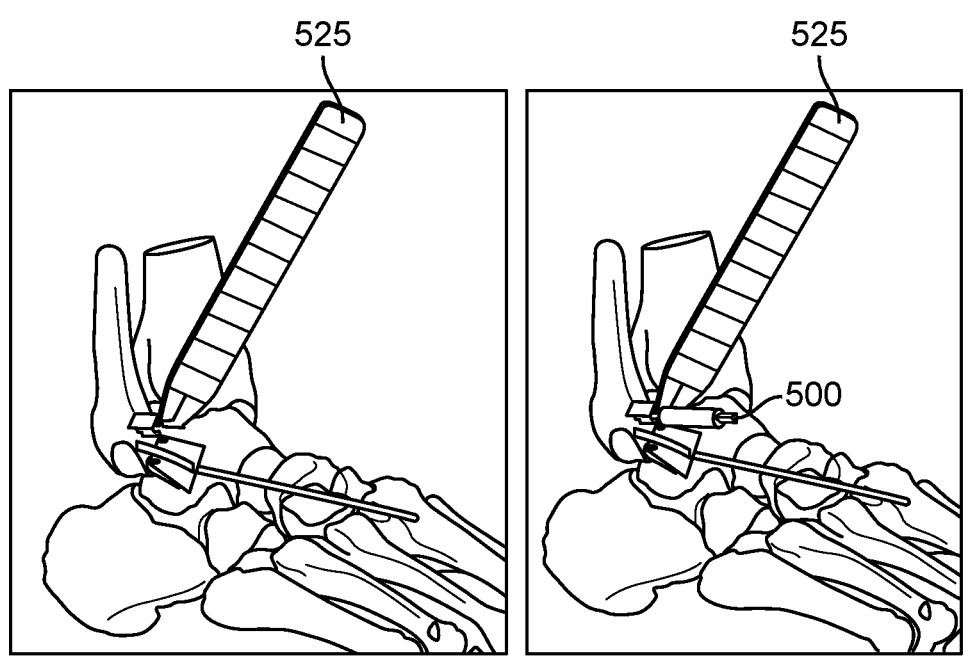
Figure 7M:
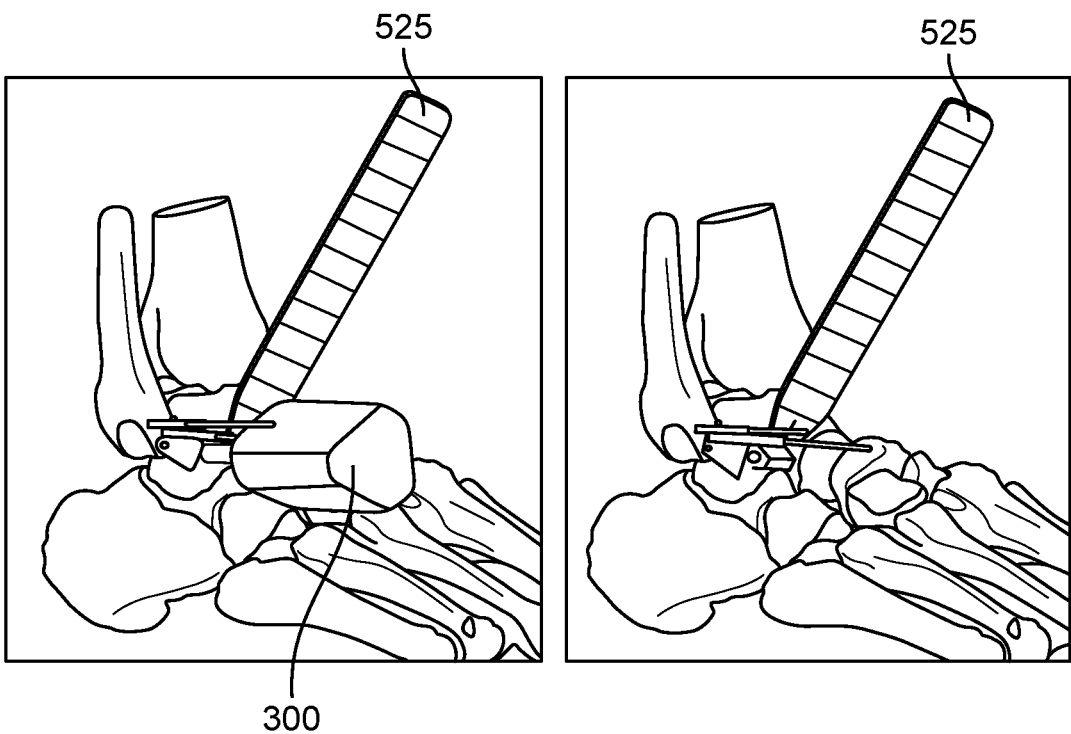
Figure 7N:
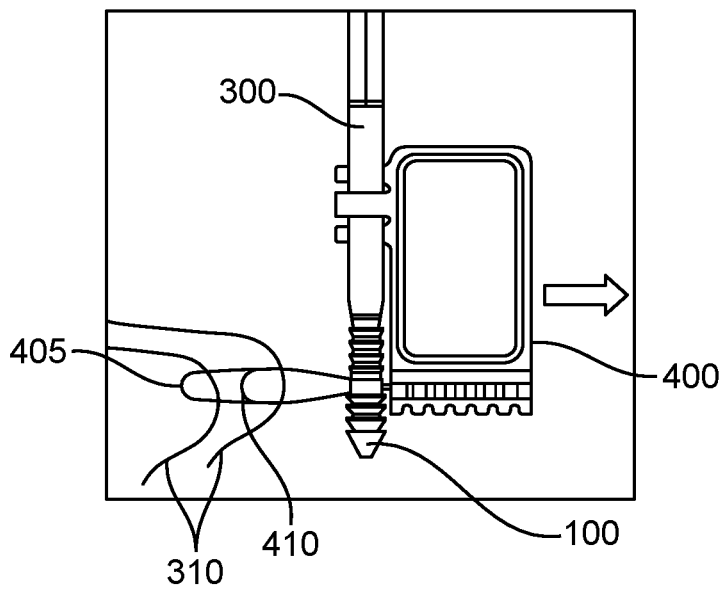
Figure 7O:
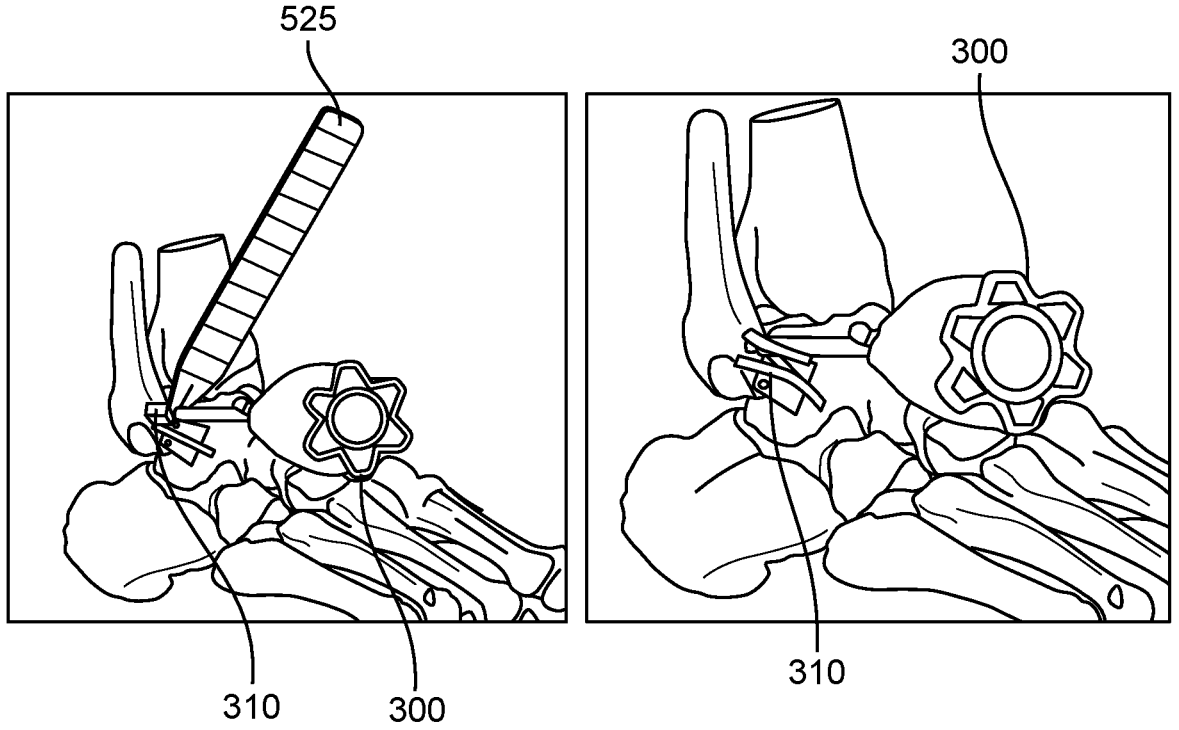
Figure 7P:
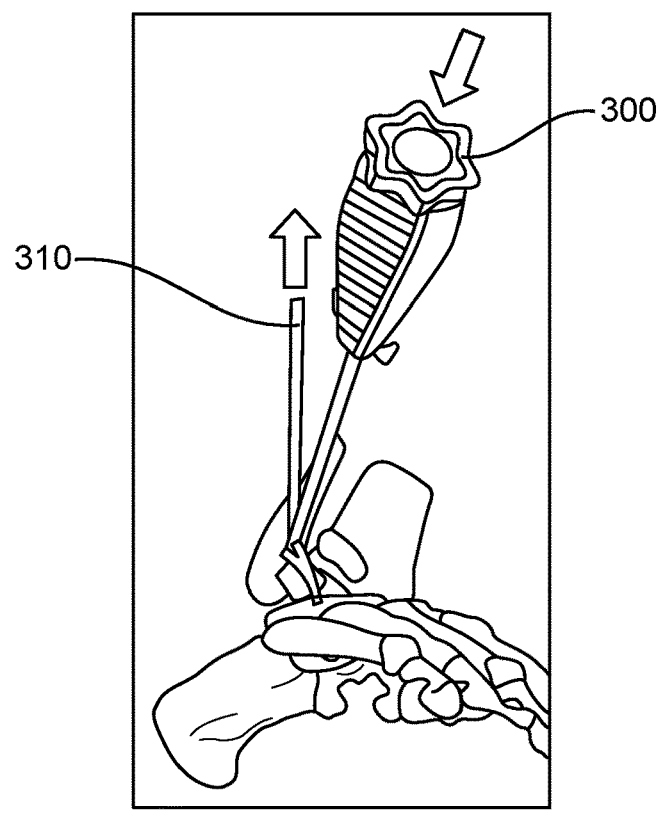
Figure 7Q:
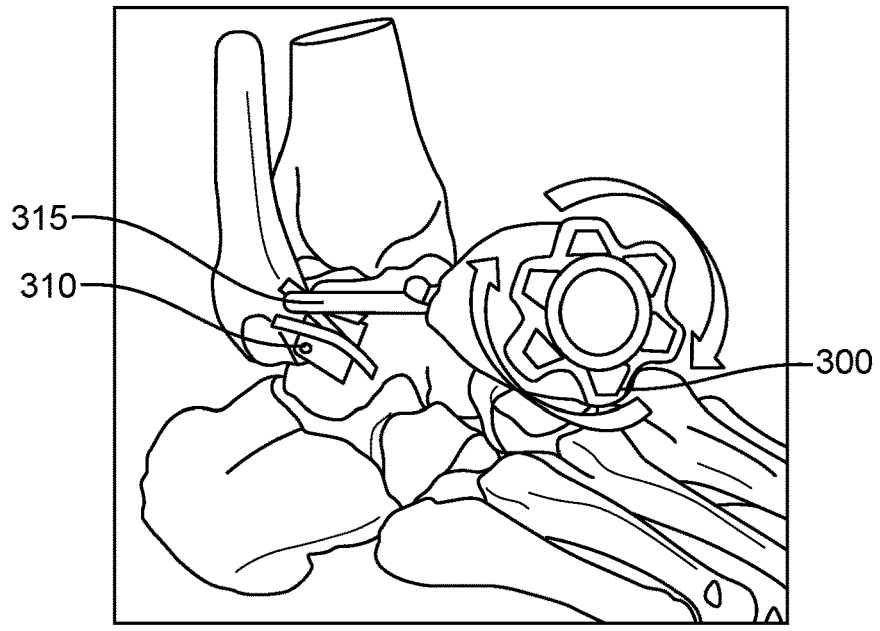
Figure 7R:
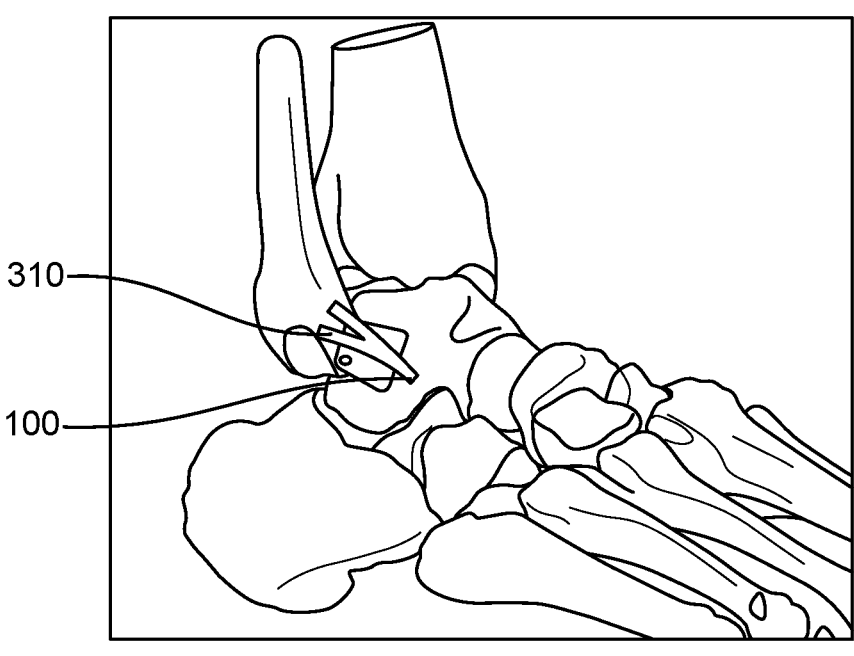

FIGS. 7A-7R illustrate an improved Brostrom repair surgical procedure using the improved suture anchor 100 of one or more embodiments.

FIG. 7A shows the surgical site for the improved Brostrom repair. Standard access and preparation methods may be used either through an open procedure or making standard anteromedial and anterolateral portals, and debriding the joint. Shown is the target surgical site 700, the talus 705, and the fibula 710. Also shown is a curved suture needle 750, and a suture 310.

FIG. 7B shows use of an open drill guide 525 and a bone drill 500 placed on the fibula at the desired location, for example, 1 cm proximal to the tip of the distal fibula. The drill, for example the drill 500 from FIG. 5, may be drilled into the bone through the open drill guide 525 such that until the drill is properly aligned over the bone, and will not drill deeper than is required, bottoming out on the drill guide 525. The surgeon may then drill to create a pilot hole for the anchor. The collar on the drill will bottom out on the drill guide 525. at the proper depth. Then the surgeon, keeping the drill guide 525 in place, may remove the drill.

For drilling a second (or subsequent) anchor hole, a round or open drill guide may be used. For example, the open drill guide 515/520 or the round drill guide 525 may be utilized. For example, in the case of an improved Brostrom repair procedure, the drill guide may be positioned within the sinus tarsi, or at another desired location. One such suitable position may be 2 cm from the lateral process. If the open drill guide 515/520 is utilized, the guide may be orientated such that the open side is in the desired direction of the suture repair. Following orientation of a drill guide; drilling of the bone may then be completed. For example, a 4.75 mm anchor drill 500 may be used. A surgeon may drill with the 4.75 mm anchor drill 500 until it bottoms out on the drill guide at the proper depth. Optionally, a drill guide insert 510 may be utilized with a 4.75 mm cannulated drill 505 to aid in drilling.

Next, following anchor hole prep, the surgical broach 200 may then be inserted into the bone pilot hole. In some embodiments, the first anchor hole is not prepared with a surgical broach to prevent any sliding of the suture, as the first broach hole may act as an anchor for the entire suture network. Using a drill guide to maintain alignment, for example the open drill guide 515/520, the surgical broach 200 may be inserted through the drill guide. For instance, the 4.75 mm Surgical broach may be inserted. The surgical broach 200 may be placed on the drill guide and adjacent to the bone surface, and then struck with a mallet on the surgical broach handle until the surgical broach handle bottoms out on the drill guide. Keeping the drill guide in place, the broach may be removed. In an alternative technique, the surgical broach insertion may be accomplished without a drill guide by aligning the direction of the broach fins with the targeted suture direction and inserting the broach with the mallet until the top of the broach is just below the cortical layer of bone. The fins of the surgical broach should be aligned with the intended suture trajectory; with the direction of the wings pointing in the direction of the intended suture trajectory.

FIG. 7C shows anchor insertion. Shown is insertion of the anchor inserter, e.g. insertion device 300, into the distal fibula. The surgeon may then advance the insertion device 300 until the anchor is near the bone surface. The surgeon may utilize the markings on the insertion device shaft for visualization and proper alignment of the anchor. The surgeon may then strike the handle on the insertion device or apply pressure until the alignment markings 321/371 near the anchor 100 are fully beneath the bone surface, and the circumferential laser marking on the inserter shaft near the handle is flush with the bone. The surgeon may then remove the suture from the cleats on the insertion device handle, and may remove the inserter by pulling it back. FIG. 7D shows the suture 310 wrapped around the suture cleats 305 of the insertion device 300 to maintain tension on the suture during anchor insertion.

Following anchor hole prep and surgical broach 200 insertion, the suture anchors 100 may be inserted. The suture anchor 100 may be attached to a delivery device 300, as well as a threading tool 400 as illustrated in FIG. 7H or 7N. The suture may be threaded through the loops of the threading tool 400, and then the threading tool 400 may be pulled laterally away from the anchor, detaching it from the insertion tool 300 shaft, and pulling the sutures through the suture passage 110 of the suture anchor 100.

Next, a suture anchor 100 may be inserted, as illustrated in FIG. 7C, 7G, 7M, or 7O. The open drill guide 515 may be utilized, or the anchor may be inserted without a drill guide. Holding the free sure tails, the anchor and insertion device assembly may be inserted through the drill guide until the anchor is near the bone surface. The surgeon may utilize the laser mark indicator on the inserter to maintain proper origination of the anchor. The surgeon may themselves strike the insertion device with a mallet on the handle until the circumferential laser mark on the inserter shaft near the anchor is fully beneath the bone surface and the circumferential laser mark near the insertion shaft is flush with the open drill guide top surface. The drill guide may then be removed.

Following insertion of a suture anchor 100, the sutures may then be tensioned, as illustrated in FIG. 7J or 7P. The surgeon may pull upwards on the suture tails, evenly with increasing tension while keeping constant downward pressure on the insertion until the desired tension is reached. The surgeon may perform range of motion tests on the patient and tighten or loosen the suture tape until the desired tension is reached with the range of motion confirmation. Optionally, when tensioning the sutures or suture tape, the tails of the sutures may be placed around one of the suture cleats 305 of the insertion device 300 while pulling downwards, as illustrated in FIG. 7J, to both tension the suture and apply downwards pressure to the inserter.

Following tensioning of the sutures, the suture may then be locked in place, as illustrated in FIG. 7K or 7Q. Once the desired tension has been reached, the suture tails may be wrapped around the cleats 305 of the insertion device 300, as illustrated in FIG. 7D, to maintain tension. Holding the handle of the insertion device steady, the base of the insertion device may be rotated clockwise to turn the internal driver, and screw in the insert body of the suture anchor. As the insert body screws into the channel of the suture anchor and contacts the suture and the distal end of the suture passage, the suture will be locked into place. The insertion device may be configured such that the knob will click if over rotated, without further tightening the insertion body.

FIG. 7F-7K shows repeating of the steps of a surgical procedure for insertion of a second suture anchor, using tools and techniques disclosed herein. FIG. 7F illustrates bone drilling and insertion of the surgical broach, optionally; FIG. 7F illustrates a drilling and broaching procedure using drill guide while FIG. 7E illustrates a drilling and broaching procedure procure without drill guides; FIGS. 7H-7I illustrate threading and insertion of a suture anchor; and FIGS. 7J-7K illustrate tensioning and locking of a suture in a suture anchor.

FIGS. 7L-7Q show repeating of the steps of a surgical procedure for a third suture anchor insertion and tissue repair using surgical techniques of one or more embodiments described herein. In the case of a Bostrom repair, for example, FIGS. 7L-7Q illustrate drilling, insertion, tensioning, and locking of a third suture anchor, and suture. FIGS. 7L-7Q illustrate bone drilling and insertion of the surgical broach, optionally; FIGS. 7N-7O illustrate threading and insertion of a suture anchor; and FIGS. 7P-7Q illustrate tensioning and locking of a suture in a suture anchor.

FIG. 7R illustrates tissue repair. After placing one or more suture anchors 100, as many as are desired to complete the given procedure, in a manner as described herein, tissue repair may be accomplished. Following placement of one or more suture anchors, the tail of one suture may be pulled through the looped end of a needle, for example, a nitinol looped end of a needle device optionally provided as a component of the surgical kits disclosed herein. The needle may have a loop at one end, and a sharp point at the opposite end, and may be used to pierce soft tissue and pull a suture through the tissue. Using a needle which a suture has been threaded through, the needle may be shuttled through the tissue being repaired as necessary to attach the tissue to the suture anchors in order to complete the surgery. This process may be repeated for all suture tails and suture anchors. For example, in the case of an improved Brostrom repair procedure, once all suture tails have been shuttled through the tissue, the suture tails may be tied down so that they lie flush on the retinaculum.

FIG. 7R illustrates a completed improved Bostrom repair procedure using the suture anchors 100 of one or more embodiments, wherein a suture 310 has been threaded through each of the suture anchors 100 and the tissues of the anterior talofibular ligament to complete a repair or tightening of the ligament.

FIG. 8 shows an alternate illustration of a completed improved Bostrom repair procedure using the suture anchors 100 of one or more embodiments, wherein a suture 310 has been threaded through each of the suture anchors 100 and the tissues of the anterior talofibular ligament to complete a repair or tightening of the ligament. Relative to a traditional Bostrom repair procedure, it can be observed that the improved Bostrom repair procedure using the suture anchors 100 of one or more embodiments utilizes a suture anchor inserted into the distal fibula with a suture passage orientated at a 90-degree angle which permits the suture to pull on the anterior talofibular ligament at a natural angle when tethered to a suture anchor in the distal fibula connecting to the calcaneo fibular ligament at approximately a 90-angle relative to the anterior talofibular ligament (see FIG. 8, for example). This triangular suture path may form a "seatbelt" over the side of the ankle, and is more anatomically similar to the natural state of the talofibular ligament and the calcaneo fibular ligament, which are both naturally anchored to the distal fibula.

Relative to a traditional Bostrom repair procedure, it can be observed that some embodiments of the improved Bostrom repair procedure using the suture anchors 100 of one or more embodiments may also pull the distal end of the suture tails in the fibular anchor through the fibular bone tunnel, as is illustrated in FIG. 8. This may result in a more anatomically aligned suture, resulting in improved patient outcomes.

In an exemplary method, disclosed is a method of repairing ligaments in the ankle in a subject, the method comprising a. threading a first suture anchor with a suture, wherein the first suture anchor is the suture anchor system of claim 1; b. inserting the first suture anchor into a lateral process; c. passing the suture through a first ligament; d. threading a second suture anchor with the suture, wherein the second suture anchor is the suture anchor system of claim 1; e. inserting the second suture anchor into a distal fibula; f. tensioning the suture between the first suture anchor and the second suture anchor; g. threading a third suture anchor with the suture, wherein the third suture anchor is the suture anchor system of claim 1; h. inserting the third suture anchor into a calcaneus; i. tensioning the suture between the second suture anchor and the third suture anchor; and j. trimming the remaining suture.

The first ligament may be the anterior talofibular ligament. The method may further comprise passing the suture through a second ligament following step f. The second ligament may be the calcaneofibular ligament. The method may further comprise drilling a hole in a distal end of the fibula at approximately a 90-degree angle relative to the longitudinal axis of the second suture anchor; and passing the suture through the hole in the distal end of the fibula. The suture may pass through the fibula and exit at a direction approximately 90 degrees relative to where the suture entered the fibula. In some embodiments, the suture tails may exit through the fibular bone tunnel. In some embodiments, steps d-e are performed prior to steps a-c.

The suture anchors and suture anchor systems of one or more embodiments disclosed herein may be used for fixation of soft tissue to bone in various anatomical locations. For example, the suture anchor systems of one or more embodiments used for fixation of soft tissue to bone in the: foot and ankle; hip; knee; hand and wrist; the elbow; the shoulder; and other area.

Possible surgical indications for use of the suture anchor systems of one or more embodiments in the shoulder include: rotator cuff repair, Bankart repair, slap lesion repair, biceps tenodesis, acromio-clavicular separation repair, deltoid repair, capsular shift or capsulolabral reconstruction, and others. These procedures may be accomplished by using the suture anchor system of one or more embodiment using prior art surgical techniques, or with the improved surgical techniques described herein, for example, broaching, or tensioning sutures using knotless suture anchors.

Possible surgical indications for use of the suture anchor systems of one or more embodiments in the foot/ankle include: lateral stabilization, medial stabilization, achilles tendon repair, hallux valgus reconstruction, mid-foot reconstruction, metatarsal ligament repair/tendon repair, bunionectomy, digital tendon transfers, and others. These procedures may be accomplished by using the suture anchor system of one or more embodiment using prior art surgical techniques, or with the improved surgical techniques described herein, for example, broaching, or tensioning sutures using knotless suture anchors.

Possible surgical indications for use of the suture anchor systems of one or more embodiments in the knee include: medial collateral ligament repair, lateral collateral ligament repair, vastus medialis obliquus advancement, patellar tendon repair, posterior oblique ligament repair, iliotibial band tenodesis, joint capsule closure, and others. These procedures may be accomplished by using the suture anchor system of one or more embodiment using prior art surgical techniques, or with the improved surgical techniques described herein, for example, broaching, or tensioning sutures using knotless suture anchors.

Possible surgical indications for use of the suture anchor systems of one or more embodiments in the hand and wrist include: scapholunate ligament reconstruction, ulnar or radial collateral ligament reconstruction, and others. These procedures may be accomplished by using the suture anchor system of one or more embodiment using prior art surgical techniques, or with the improved surgical techniques described herein, for example, broaching, or tensioning sutures using knotless suture anchors.

Possible surgical indications for use of the suture anchor systems of one or more embodiments in the elbow include: biceps tendon reattachment, tennis elbow repair, ulnar or radial collateral ligament reconstruction, lateral epicondylitis repair, and others. These procedures may be accomplished by using the suture anchor system of one or more embodiment using prior art surgical techniques, or with the improved surgical techniques described herein, for example, broaching, or tensioning sutures using knotless suture anchors.

Possible surgical indications for use of the suture anchor systems of one or more embodiments in the hip include: capsular repair, acetabular labral repair, and others. These procedures may be accomplished by using the suture anchor system of one or more embodiment using prior art surgical techniques, or with the improved surgical techniques described herein, for example, broaching, or tensioning sutures using knotless suture anchors.

Example: Rotator Cuff Repair

The suture anchors and suture anchor systems of one or more embodiments disclosed herein may be used to facilitate a rotator cuff repair procedure.

Medial Row Anchor Insertion

A surgeon drills or punches a hole for the first medial row anchor using a surgical drill, for example, using the suture anchor drill 500. A surgical broach is inserted into the bone pilot hole, aligning the wings of the broach with the intended suture trajectory, and malleted in until the broach is just below the surface of the bone. A suture anchor with a 45 degree suture passage is utilized, and a surgical broach with wings originated at 45 degrees is utilized. In some embodiments, broaching may be skipped. Next, a surgeon orients the suture such that it is lined up to correctly match the lateral row suture trajectory, and insert the anchor into the hole. This process is repeated for $2^{nd}$ medial row anchor. Two 4.5 mm outer diameter suture anchors preloaded with at least one suture tape are utilized. A benefit of broaching on the medial row may include smoothing the bone edge to improve the suture trajectory. Following medial row anchor insertion, the suture tails are used to stitch the soft tissue.

Lateral Row Anchor Insertion

A surgeon drills or punches a hole drill or punch a hole for the lateral row anchor, for example, using the suture anchor drill 500. A surgical broach may be inserted into the bone pilot hole, aligning the wings of the broach with the intended suture trajectory, and malleted in until the broach is just below the surface of the bone. A suture anchor with a 45 degree suture passage is utilized, and a surgical broach with wings originated at 45 degrees may be utilized. Following stitching of the tissue with a suture, one suture tail from each of the medial row anchors is inserted through the central window via use of the pull tab on the suture tail threading tool. The pull tab is discarded after use. The anchor is orientated and with loaded suture such that it is aligned with the medial row and the natural trajectory of the suture tape. The lateral row anchor and tension sutures are tensioned as needed before locking in place. This process is repeated for the $2^{nd}$ lateral row anchor. Then, 5.5 mm outer diameter anchors with a suture tape threading pull tab preloaded onto them to aid with suture loading are utilized. The sutures are then tensioned and secured into place with the anchor body insert, driven by the internal driver on the suture anchor insertion tool. Broaching is utilized to aid in suture tensioning, and to smooth the bone edge to improve the suture trajectory.

Example: Gamekeeper Thumb Surgery-Thumb UCL Repair

The suture anchors and suture anchor systems of one or more embodiments disclosed herein may be used to facilitate a thumb UCL repair procedure.

A surgeon may place a guidewire to the bone on the proximal phalanx. A second guidewire may be placed just proximal to the UCL on the metacarpal. Both guidewires may be drilled with a 3.5 mm cannulated drill bit and drill guide. A 1.8 mm cannulated drill bit may be utilized to accommodate smaller anatomy when needed. A surgical broach may be inserted into the bone pilot holes, aligning the wing of the broach with the intended suture trajectory, and malleted in until the broach is just below the surface of the bone. A dual wing 180 degree surgical broach is utilized, and a suture anchor with a suture passage orientated at 180 degrees is utilized. A suture anchor is placed into an anchor insertion tool Suture tape is then threaded through the suture passage of the suture anchor using the suture trading tool with pull tab. Once the suture anchor is threaded, the pull tab is disposed of. The suture tails are removed from the surgical site by wrapping them around the suture cleats on the anchor insertion tool. The first suture anchor is then inserted into the proximal phalanx with the suture anchor insertion device, aligning the suture passage with the intended suture trajectory, the suture extending towards the UCL on the metacarpal. Suture tails extend upwards from the central window of the suture anchor on opposites sides of the anchor body, in their respective suture grooves. The suture is then pulled through the MCL to facilitate the repair, and the suture tape is tensioned. The suture tape is then brought over the ligament, threaded into a second suture anchor, and inserted into the suture anchor insertion device, with the suture threading tool. The pull tab of the suture threading tool may then be discarded. The thumb is then flexed 30 degrees, and the second suture anchor is then inserted into the broached metacarpal pilot hole with the suture anchor insertion device, aligning the suture passage with the intended suture trajectory, the suture extending towards the proximal phalanx. The suture is then tensioned between the two suture anchors, and any remaining suture is cut flush with the anchor to complete the repair. A 3.5 mm suture anchor approximately 8.5 mm in length, along with 1.3 mm suture tape are utilized.

Example: Achilles Tendon Repair

The suture anchors and suture anchor systems of one or more embodiments disclosed herein may be used to facilitate an Achilles tendon repair procedure.

A surgeon may place a guidewire to the bone on the calcaneus. The guidewire may be drilled with a 4 mm cannulated drill bit and drill guide. A surgical broach may be inserted into the bone pilot hole aligning the wing of the broach with the intended suture trajectory, and malleted in until the broach is just below the surface of the bone. A dual wing 180 degree surgical broach is utilized, and a suture anchor with a suture passage orientated at 180 degrees is utilized. The drilling and broaching process is repeated to form 2 broached bone pilot holes.

The heel is flexed 15 degrees, and the suture is then pulled through a first suture insertion site in the Achilles tendon in a helical manner, wrapping around an exterior side of the tendon for at least 3 rotations through and around the tendon going up, and then again for at least for at least 3 rotations through and around the tendon going down. The suture is then pulled through a second suture insertion site in the Achilles tendon in a helical manner, wrapping around an exterior side of the tendon for at least 3 rotations through and around the tendon going up, and then again for at least for at least 3 rotations through and around the tendon going down. The suture is then pulled through a third suture insertion site in the Achilles tendon in a helical manner, wrapping around an exterior side of the tendon for at least 3 rotations through and around the tendon going up, and then again for at least for at least 3 rotations through and around the tendon going down. Following attachment of the suture to the Achilles tendon, there should be two sets of suture tails on each side of the tendon.

A suture anchor is placed into an anchor insertion tool suture tape and is then threaded with the first set of suture tails through the suture passage of the suture anchor using the suture trading tool with pull tab. Once the suture anchor is threaded, the pull tab is disposed of. The suture tails are removed from the surgical site by wrapping them around the suture cleats on the anchor insertion tool. The first suture anchor is then inserted into the first bone pilot hole in the calcaneus, carefully aligning the suture groove with the direction that the suture pulls on the tendon. Suture tails extend upwards from the central window of the suture anchor on opposites sides of the anchor body, in their respective suture grooves. The suture tails may then be tensioned one by one, and secured using the anchor body insert, using the internal driver on the anchor insertion tool.

A second suture anchor is placed into an anchor insertion tool suture tape and is then threaded with the second set of suture tails through the suture passage of the suture anchor using the suture trading tool with pull tab. Once the suture anchor is threaded, the pull tab is disposed of. The suture tails are removed from the surgical site by wrapping them around the suture cleats on the anchor insertion tool. The second suture anchor is then inserted into the second bone pilot hole in the calcaneus, carefully aligning the suture groove with the direction that the suture pulls on the tendon. Suture tails extend upwards from the central window of the suture anchor on opposites sides of the anchor body, in their respective suture grooves. The suture tails may then be tensioned one by one, and secured using the anchor body insert, using the internal driver on the anchor insertion tool.

As used herein, the term "approximately" means within 15% of a given stated numerical value for a parameter, variable, dimension, and the like.

As will be understood by one of ordinary skill in the art, any of the anchors, inserts, sutures, and delivery devices may be combined with one another or substituted for another and thus any number of combinations may be used. Additionally, various features of an anchor system have been described herein including anchor tip configurations, insert tip configurations, channel configurations, suture passage configurations, suture groove configurations, bone engaging ridges, suture types and numbers, delivery device configurations, driver tip configurations, and device coupler configurations. One of ordinary skill in the art will appreciate that these features may be combined with one another or substituted for another and thus any number of combinations may be used.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of repairing ligaments in an ankle in a subject, the method comprising:

inserting a first suture anchor into a first bone, wherein a suture is threaded through the first suture anchor and the first bone is the lateral process;

passing the suture through a first ligament;

threading the suture through a second suture anchor;

inserting the second suture anchor into a second bone;

tensioning the suture between the first suture anchor and the second suture anchor;

threading a third suture anchor with the suture;

inserting the third suture anchor into a third bone;

tensioning the suture between the second suture anchor and the third suture anchor; and trimming the remaining suture.

2. The method of claim 1, wherein the first suture anchor, the second suture anchor, the third suture anchor, or any combination thereof, comprises:

a. an anchor body having a proximal end, a distal end, a longitudinal axis, a first lateral side extending between the proximal and distal end, and a second lateral side extending between the proximal and distal end;

b. a suture passage comprising a proximal surface and a distal surface and extending through the anchor body from a first opening in the first lateral side to a second opening in the second lateral side;

c. a channel defined within the anchor body and extending along the longitudinal axis of the anchor body from a proximal opening in the proximal end of the anchor body to an opening in the proximal surf ace of the suture passage; and d. an insert comprising an insert body having a proximal end and a distal end, wherein the insert is configured to translate longitudinally within the channel between the proximal end of the anchor body and the distal surface of the suture passage.

3. The method of claim 1, wherein the first suture anchor, the second suture anchor, the third suture anchor, or any combination thereof, comprises:

a. a plurality of distal ridges disposed on an anchor body, wherein the plurality of distal ridges is proximal to a distal end and distal to a suture passage; and b. one or more proximal ridges disposed on the anchor body, wherein the one or more proximal ridges are distal to a proximal end and proximal to the suture passage.

4. The method of claim 1, wherein the first suture anchor, the second suture anchor, the third suture anchor, or any combination thereof, comprises a suture groove disposed along an anchor body at least partially between a suture passage and a proximal end of the anchor body, the suture groove configured to receive a suture therein.

5. The method of claim 1, wherein the first suture anchor, the second suture anchor, the third suture anchor, or any combination thereof, comprises a distal surface of a suture passage that is v-shaped and has a first lateral plane extending from a first opening towards a central normal plane and a second lateral plane extending from a second opening towards the central normal plane, the central normal plane being substantially perpendicular to a longitudinal axis of an anchor body.

6. The method of claim 1, wherein the first suture anchor, the second suture anchor, the third suture anchor, or any combination thereof, comprises a distal surface of a suture passage that is substantially flat and substantially perpendicular to a longitudinal axis of an anchor body.

7. The method of claim 2, wherein the first suture anchor, the second suture anchor, the third suture anchor, or any combination thereof, comprises at least a portion of a distal surface of a suture passage which comprises a convex curvature extending proximally towards an opening in a proximal surf ace of the suture passage.

8. The method of claim 1, wherein the first ligament is the anterior talofibular ligament.

9. The method of claim 1, further comprising passing the suture through a second ligament after threading the third suture anchor with the suture.

10. The method of claim 9, wherein the second ligament is the calcaneofibular ligament.

11. The method of claim 1, wherein the first suture anchor is inserted approximately 2 cm into the lateral process.

12. The method of claim 1, wherein the second bone is a fibula.

13. The method of claim 12, further comprising drilling a hole in a distal end of the fibula at approximately a 90 degree angle relative to the longitudinal axis of the second suture anchor; and passing the suture through the hole in the distal end of the fibula.

14. The method of claim 12, wherein the suture passes through the fibula and exits at a direction approximately 90 degrees relative to where the suture entered the fibula.

15. The method of claim 12, where the second suture anchor is inserted 1 cm proximal to the tip of the distal fibula.

16. The method of claim 1, wherein the third bone is a calcaneus.

17. The method of claim 1, wherein the ligament repair is a Brostrom repair.

18. The method of claim 1, wherein threading the suture through the second suture anchor and inserting the second suture anchor into the second bone is performed prior to inserting the first suture anchor into the first bone.

19. The method of claim 18, wherein threading the suture through the third suture anchor and inserting the third suture anchor into the third bone is performed prior to inserting the first suture anchor into the first bone.

\* \* \* \* \*